US006904909B2

(12) United States Patent
Andreas et al.

(10) Patent No.: US 6,904,909 B2
(45) Date of Patent: Jun. 14, 2005

(54) METHODS AND DEVICES FOR USE IN PERFORMING PULMONARY PROCEDURES

(75) Inventors: Bernard H. Andreas, Redwood City, CA (US); Sunmi Chew, San Jose, CA (US); Anton J. Fields, San Francisco, CA (US); Ronald R. Hundertmark, San Mateo, CA (US); Alan R. Rapacki, Redwood City, CA (US); Peter M. Wilson, Foster City, CA (US)

(73) Assignee: Emphasys Medical, Inc., Redwood City, CA (US)

( * ) Notice: Subject to any disclaimer, the term of this patent is extended or adjusted under 35 U.S.C. 154(b) by 281 days.

(21) Appl. No.: 10/303,318

(22) Filed: Nov. 22, 2002

(65) Prior Publication Data

US 2003/0075170 A1 Apr. 24, 2003

Related U.S. Application Data

(63) Continuation of application No. 09/797,910, filed on Mar. 2, 2001, which is a continuation-in-part of application No. 09/519,735, filed on Mar. 4, 2000.

(51) Int. Cl.⁷ .......................... A61M 15/00; A61M 16/00
(52) U.S. Cl. .................................................. 128/200.24
(58) Field of Search ...................... 604/27; 128/200.24, 128/200; 600/407

(56) References Cited

U.S. PATENT DOCUMENTS

| | | | |
|---|---|---|---|
| 2,981,254 A | 4/1961 | Vanderbilt | 128/350 |
| 3,657,744 A | 4/1972 | Ersek | 128/334 |
| 3,788,327 A | 1/1974 | Donowitz et al. | 128/350 |
| 3,874,388 A | 4/1975 | King et al. | 128/334 |
| 4,014,318 A | 3/1977 | Dockum et al. | 128/1 |
| 4,086,665 A | 5/1978 | Poirier | 623/1 |
| 4,212,463 A | 7/1980 | Repinski et al. | 273/418 |
| 4,250,873 A | 2/1981 | Bonnet | 600/104 |
| 4,302,854 A | 12/1981 | Runge | 3/1.7 |
| 4,477,930 A | 10/1984 | Totten et al. | 3/1.5 |
| 4,710,192 A | 12/1987 | Liotta et al. | 623/1 |
| 4,732,152 A | 3/1988 | Wallsten et al. | 128/343 |
| 4,759,758 A | 7/1988 | Gabbay | 623/2 |
| 4,795,449 A | 1/1989 | Schneider et al. | 604/329 |
| 4,808,183 A | 2/1989 | Panje | 623/9 |
| 4,819,664 A | 4/1989 | Nazari | 128/207.15 |
| 4,830,003 A | 5/1989 | Wolff et al. | 128/343 |
| 4,832,680 A | 5/1989 | Haber et al. | 600/31 |
| 4,846,836 A | 7/1989 | Reich | 623/11 |
| 4,850,999 A | 7/1989 | Planck | 623/1 |
| 4,852,568 A | 8/1989 | Kensey | 128/325 |
| 4,877,025 A | 10/1989 | Hanson | 128/107.16 |
| 4,934,999 A | 6/1990 | Bader | 600/29 |
| 4,968,294 A | 11/1990 | Salama | 600/30 |
| 5,061,274 A | 10/1991 | Kensey | 606/213 |

(Continued)

FOREIGN PATENT DOCUMENTS

| | | |
|---|---|---|
| EP | 0621 015 B1 | 10/1994 |
| EP | 0621 015 A1 | 10/1994 |
| EP | 1 078 601 A2 | 2/2001 |

(Continued)

OTHER PUBLICATIONS

IL Jishi et al., "Selective Bronchial Occlusion for Treatment of Bullous Interstitial Emphysema and Bronchopleural Fistula." *J. of Pediatric Surgery*, 29:12, 1994: 1545–1547.

(Continued)

*Primary Examiner*—Henry Bennett
*Assistant Examiner*—Sabrina Dagostino
(74) *Attorney, Agent, or Firm*—Fish & Richardson P.C.; Fred C. Hernandez

(57) ABSTRACT

An implantable flow control element is provided which prevents air from entering an isolated portion of a patient's lung. The element may permit air to escape from the isolated portion so that the element acts like a valve. Systems for implanting pulmonary devices are also provided.

38 Claims, 26 Drawing Sheets

U.S. PATENT DOCUMENTS

| | | | |
|---|---|---|---|
| 5,116,360 A | 5/1992 | Pinchuk et al. | 623/1 |
| 5,116,564 A | 5/1992 | Jansen et al. | 264/255 |
| 5,123,919 A | 6/1992 | Sauter et al. | 623/2 |
| 5,151,105 A | 9/1992 | Kwan-Gett | 623/1 |
| 5,161,524 A | 11/1992 | Evans | 128/203.15 |
| 5,306,234 A | 4/1994 | Johnson | 604/49 |
| 5,352,240 A | 10/1994 | Ross | 623/2 |
| 5,358,518 A | 10/1994 | Camilli | 623/2 |
| 5,366,478 A | 11/1994 | Brinkerhoff et al. | 660/213 |
| 5,382,261 A | 1/1995 | Palmaz | 606/158 |
| 5,392,775 A | 2/1995 | Adkins et al. | 128/207.16 |
| 5,409,019 A | 4/1995 | Wilk | 128/898 |
| 5,411,507 A | 5/1995 | Heckele | 606/108 |
| 5,411,552 A | 5/1995 | Andersen et al. | 623/2 |
| 5,413,599 A | 5/1995 | Imachi et al. | 623/2 |
| 5,417,226 A | 5/1995 | Juma | 128/885 |
| 5,445,626 A | 8/1995 | Gigante | 604/349 |
| 5,486,154 A | 1/1996 | Kelleher | 600/104 |
| 5,499,995 A | 3/1996 | Teirstein | 606/192 |
| 5,500,014 A | 3/1996 | Quijano et al. | 623/2 |
| 5,562,608 A | 10/1996 | Sekins | 604/20 |
| 5,645,565 A | 7/1997 | Rudd et al. | 606/213 |
| 5,660,175 A | 8/1997 | Dayal | 128/207.15 |
| 5,662,713 A | 9/1997 | Andersen et al. | 623/12 |
| 5,683,451 A | 11/1997 | Lenker et al. | 623/1 |
| 5,697,968 A | 12/1997 | Rogers et al. | 623/1 |
| 5,755,770 A | 5/1998 | Ravenscroft | 623/1 |
| 5,800,339 A | 9/1998 | Salama | 600/29 |
| 5,840,081 A | 11/1998 | Andersen et al. | 623/2 |
| 5,851,232 A | 12/1998 | Lois | 623/1 |
| 5,855,587 A | 1/1999 | Hyon et al. | 606/188 |
| 5,855,597 A | 1/1999 | Jayaraman | 623/1 |
| 5,855,601 A | 1/1999 | Bessler et al. | 623/2 |
| 5,944,738 A | 8/1999 | Amplatz et al. | 606/213 |
| 5,947,997 A | 9/1999 | Pavcnik et al. | 606/213 |
| 5,954,766 A | 9/1999 | Zadno-Azizi et al. | 623/2 |
| 5,957,949 A | 9/1999 | Leonhardt et al. | 606/194 |
| 5,976,174 A | 11/1999 | Ruiz | 606/213 |
| 5,984,965 A | 11/1999 | Knapp et al. | 623/12 |
| 6,007,575 A | 12/1999 | Samuels | 623/1 |
| 6,009,614 A | 1/2000 | Morales | 29/516 |
| 6,020,380 A | 2/2000 | Killian | 514/570 |
| 6,022,312 A | 2/2000 | Chaussy et al. | 600/29 |
| 6,027,525 A | 2/2000 | Suh et al. | 623/1 |
| 6,051,022 A | 4/2000 | Cai et al. | 623/2 |
| 6,068,635 A | 5/2000 | Gianotti | 606/108 |
| 6,068,638 A | 5/2000 | Makower | 606/159 |
| 6,077,291 A | 6/2000 | Das | 606/213 |
| 6,083,255 A | 7/2000 | Laufer et al. | 607/96 |
| 6,123,663 A | 9/2000 | Rebuffat | |
| 6,135,729 A | 10/2000 | Aber | 417/420 |
| 6,135,991 A | 10/2000 | Muni et al. | 604/509 |
| 6,141,855 A | 11/2000 | Morales | 29/516 |
| 6,162,245 A | 12/2000 | Jayaraman | 623/1.15 |
| 6,168,614 B1 | 1/2001 | Andersen et al. | 623/1 |
| 6,174,323 B1 | 1/2001 | Biggs et al. | 606/232 |
| 6,183,520 B1 | 2/2001 | Pintauro et al. | 623/23.64 |
| 6,200,333 B1 | 3/2001 | Laufer | 607/96 |
| 6,206,918 B1 | 3/2001 | Campbell et al. | 623/2.32 |
| 6,234,996 B1 | 5/2001 | Bagaoisan et al. | 604/97.01 |
| 6,240,615 B1 | 6/2001 | Kimes et al. | 29/516 |
| 6,245,102 B1 | 6/2001 | Jayaraman | 623/1.15 |
| 6,258,100 B1 | 7/2001 | Alferness et al. | 606/108 |
| 6,270,527 B1 | 8/2001 | Campbell et al. | 623/2.18 |
| 6,287,290 B1 | 9/2001 | Perkins et al. | 604/516 |
| 6,293,951 B1 * | 9/2001 | Alferness et al. | 606/108 |
| 6,302,893 B1 | 10/2001 | Limon et al. | 606/108 |
| 6,312,407 B1 | 11/2001 | Zadno-Azizi et al. | 604/103.03 |
| 6,325,777 B1 | 12/2001 | Zadno-Azizi et al. | 607/97.01 |
| 6,325,778 B1 | 12/2001 | Zadno-Azizi et al. | 604/99.02 |
| 6,327,772 B1 | 12/2001 | Zadno-Azizi et al. | 29/557 |
| 6,328,689 B1 | 12/2001 | Gonzalez | 600/37 |
| 6,355,014 B1 | 3/2002 | Zadno-Azizi et al. | 604/99.02 |
| 6,398,775 B1 | 6/2002 | Perkins et al. | 604/514 |
| 6,402,754 B1 | 6/2002 | Gonzalez | 606/69 |
| 6,416,554 B1 | 7/2002 | Alferness et al. | 623/23.65 |
| 6,458,076 B1 | 10/2002 | Pruitt | 600/146 |
| 6,485,407 B2 | 11/2002 | Alferness et al. | 600/37 |
| 6,491,706 B1 | 12/2002 | Alferness et al. | 606/157 |
| 6,493,589 B1 | 12/2002 | Medhkour et al. | 607/99 |
| 6,510,846 B1 | 1/2003 | O'Rourke | 128/200.21 |
| 6,527,761 B1 | 3/2003 | Soltesz et al. | 604/516 |
| 2001/0025132 A1 | 9/2001 | Alferness et al. | 600/37 |
| 2001/0037808 A1 | 11/2001 | Deem et al. | 128/200.24 |
| 2001/0041906 A1 | 11/2001 | Gonzalez | 606/191 |
| 2001/0051799 A1 | 12/2001 | Ingenito | 604/516 |
| 2001/0052344 A1 | 12/2001 | Doshi | 128/207 |
| 2001/0056274 A1 | 12/2001 | Perkins et al. | 604/516 |
| 2002/0007831 A1 | 1/2002 | Davenport et al. | 128/200.24 |
| 2002/0026233 A1 | 2/2002 | Shaknovich | 623/1.24 |
| 2002/0062120 A1 | 5/2002 | Perkins et al. | 604/516 |
| 2002/0077593 A1 | 6/2002 | Perkins et al. | 604/96.01 |
| 2002/0077696 A1 | 6/2002 | Zadno-Azizi et al. | 623/1.24 |
| 2002/0087153 A1 | 7/2002 | Roschak et al. | 606/27 |
| 2002/0095209 A1 | 7/2002 | Zadno-Azizi et al. | 623/1.24 |
| 2002/0111619 A1 | 8/2002 | Keast et al. | 606/41 |
| 2002/0111620 A1 | 8/2002 | Cooper et al. | 606/41 |
| 2002/0112729 A1 | 8/2002 | DeVore et al. | 128/207.15 |
| 2002/0138135 A1 | 9/2002 | Duerig et al. | 623/1.24 |
| 2003/0018327 A1 | 1/2003 | Truckai et al. | 606/32 |
| 2003/0018344 A1 | 1/2003 | Kaji et al. | 606/130 |
| 2003/0050648 A1 | 3/2003 | Alferness et al. | 606/108 |
| 2003/0083671 A1 | 5/2003 | Rimbaugh et al. | 606/108 |

FOREIGN PATENT DOCUMENTS

| | | |
|---|---|---|
| EP | 01/28433 A1 | 4/2001 |
| EP | 1 151 729 A1 | 11/2001 |
| GB | 2324729 | 4/1998 |
| RU | 2140211 | 10/1999 |
| SU | 852321 | 7/1981 |
| SU | 1371700 | 2/1988 |
| SU | 1593651 | 9/1990 |
| WO | 94/26175 | 11/1994 |
| WO | 95/32018 | 11/1995 |
| WO | 96/34582 | 11/1996 |
| WO | 97/44085 | 11/1997 |
| WO | 98/00840 | 1/1998 |
| WO | 98/19633 | 5/1998 |
| WO | 98/39047 | 9/1998 |
| WO | 98/44854 A1 | 10/1998 |
| WO | 98/48706 | 11/1998 |
| WO | 99/01076 | 1/1999 |
| WO | 99/13801 | 3/1999 |
| WO | 99/26692 | 6/1999 |
| WO | 99/32040 | 7/1999 |
| WO | 99/42059 | 8/1999 |
| WO | 99/42161 | 8/1999 |
| WO | 99/64109 A1 | 12/1999 |
| WO | 00/15149 | 3/2000 |
| WO | 00/42950 | 7/2000 |
| WO | 00/51510 | 9/2000 |
| WO | 00/62699 | 10/2000 |
| WO | 00/78386 A1 | 12/2000 |
| WO | 00/78407 A1 | 12/2000 |
| WO | 01/02042 A1 | 1/2001 |
| WO | 01/03642 A1 | 1/2001 |
| WO | 01/05334 A1 | 1/2001 |
| WO | 01/10313 A1 | 2/2001 |
| WO | 01/10314 A2 | 2/2001 |
| WO | 01/12104 A1 | 2/2001 |
| WO | 01/13839 A1 | 3/2001 |

| WO | 01/13908 A2 | 3/2001 |
| WO | 01/45590 A2 | 6/2001 |
| WO | 01/49213 A2 | 7/2001 |
| WO | 01/54585 A1 | 8/2001 |
| WO | 01/54625 A1 | 8/2001 |
| WO | 01/54685 A1 | 8/2001 |
| WO | 01/66190 A2 | 9/2001 |
| WO | 01/74271 A1 | 10/2001 |
| WO | 01/87170 A1 | 11/2001 |
| WO | 01/89366 A2 | 11/2001 |
| WO | 01/95786 A2 | 12/2001 |
| WO | 02/05884 A2 | 1/2002 |
| WO | 02/22072 A2 | 3/2002 |
| WO | 02/32333 A1 | 4/2002 |
| WO | 02/34322 A2 | 5/2002 |
| WO | 02/38038 A2 | 5/2002 |
| WO | 02/47575 A2 | 6/2002 |
| WO | 02/056794 A2 | 7/2002 |
| WO | 02/064045 A1 | 8/2002 |
| WO | 02/064190 A3 | 8/2002 |
| WO | 02/064190 A2 | 8/2002 |
| WO | 02/069823 A3 | 9/2002 |
| WO | 02/069823 A2 | 9/2002 |
| WO | 02/094087 A1 | 11/2002 |
| WO | 03/022124 A2 | 3/2003 |

OTHER PUBLICATIONS

Article: "Autocath® 100—Nonsurgical, Intraurethral Bladder Control Device for Incontinent and Retentive Women—Dr. Kulisz's Development".

Derwent citing Russian Patent No. RU 2140211, published Oct. 27, 1999, for: "Method of surgical treatment of patients with pathology of respiratory organs complicated with pulmonary hemorrhages".

Derwent citing Soviet Union Patent No. SU 852–321, published Jul. 8, 1981, for: "Treatment for acute pulmonary and pleural disease in children—by pneumo–abcessotomy simultaneous with occlusion of affected lung part".

Derwent# 007607249 WPI Acc No: 1988–241181/198834 (citing Russian Application No. SU4026409, published Feb. 21, 1986), Russian Patent No. SU 1371700.

Derwent# 008650867 WPI Acc No: 1991–154896/199121 (citing Russian Application No. SU4280143, published Jul. 7, 1987), Russian Patent No. SU 1593651.

Harris et al., "The Experimental Production in Dogs of Emphysema with Associated Asthmatic Syndrome by Means of an Intratracheal Ball Valve." *J. Exp Med* 30:1919; 75–88.

Lewis et al. "Pulmonary Interstitial Emphysema: Selective Broncial Occlusion with a Swan–Ganz Catheter." *Archives of Disease in Childhood*, 63:1988, 313–315.

Mathew et al. "Selective bronchial obstruction for treatment of bullous interstitial emphysema." *J. of Ped.* 96:1980, 475–477.

Okada et al. "Emergent Bronchofiberoptic Bronchial Occlusion for Intractable Pneumothorax with Sever Emphysema." *The Jap. J. of Thor. And Cardio. Sur.* 46:11, 1998 1078–1081.

Puhakka et al. "Acute Bronchial Obstruction: An Experimental Rabbit Model Study." *Int. J. of Pediatric Otorhinolaryngology.* 18:1989, 107–118.

Snider et al., *The Definition of Emphysema*: Report of the National Heart Lung and Blood Institute, Division of Lung Diseases Workshop, *Am. Rev. Respir. Dis.*, 132:182–185, 1985.

Woodring et al. "Pneumothorax ex Vacuo" CHEST, 100:1102–1124 (1996).

* cited by examiner

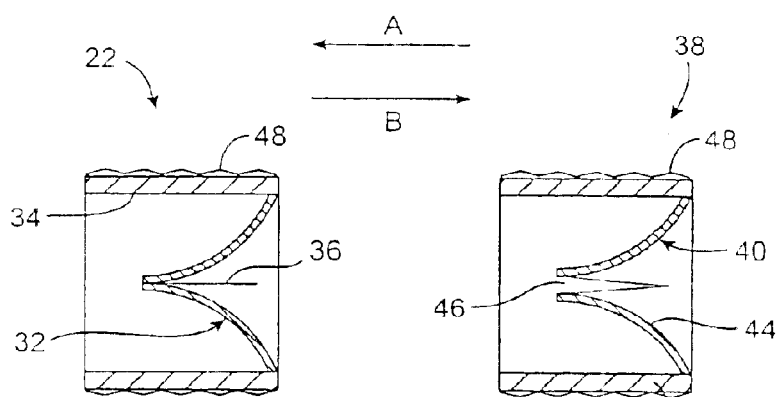
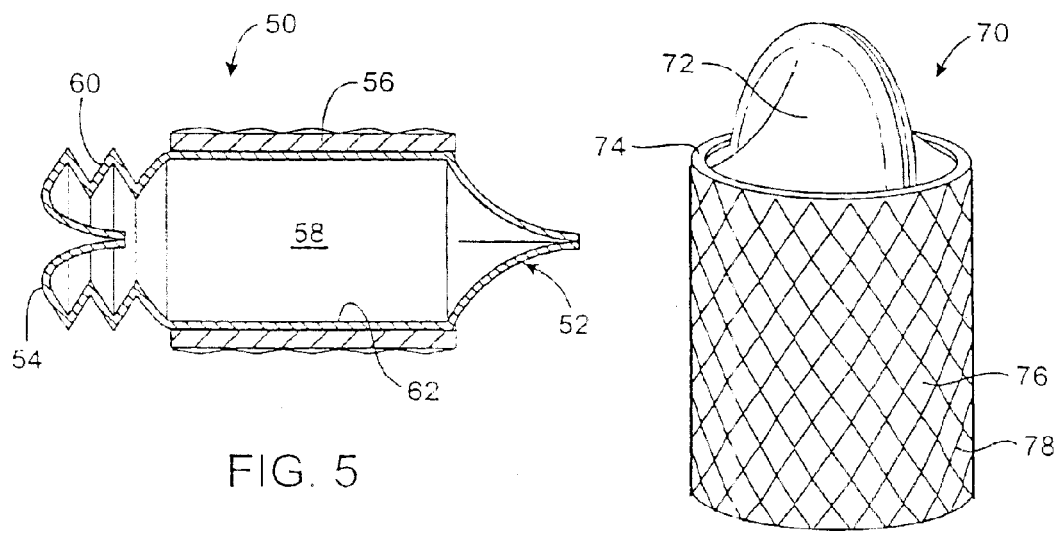

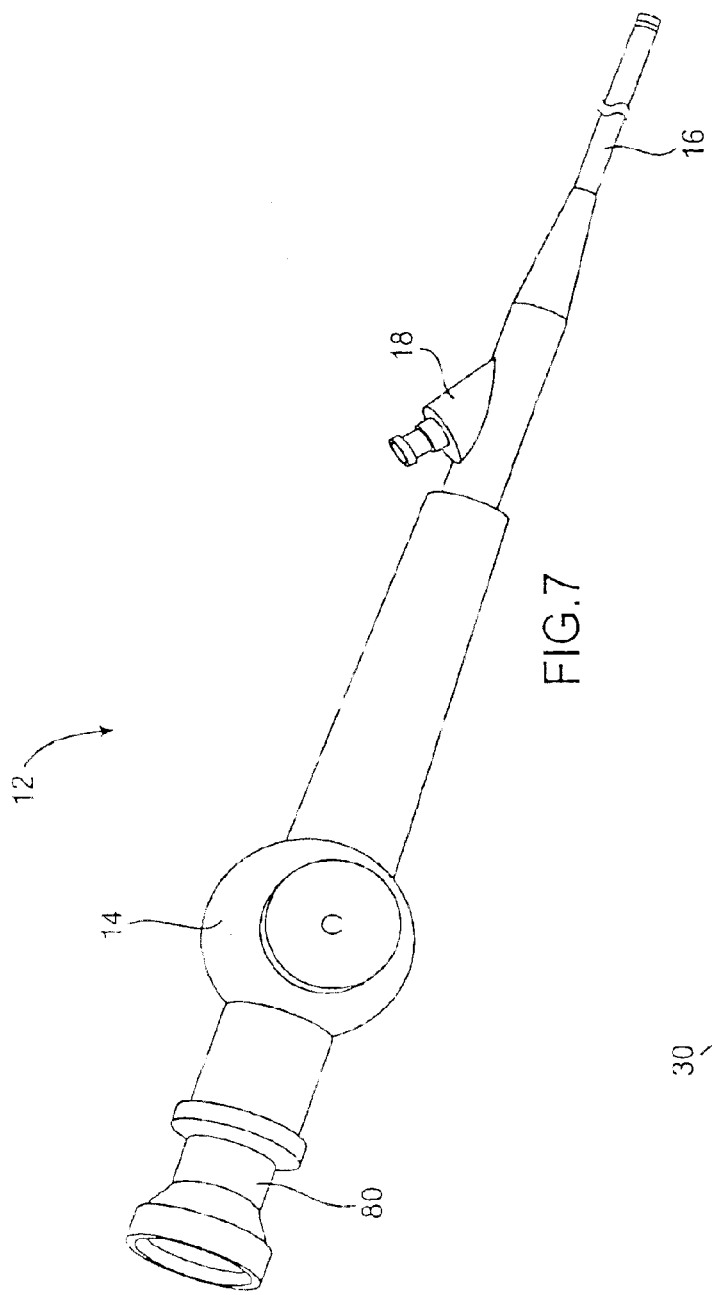
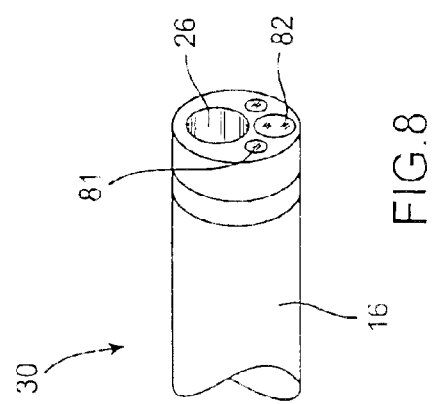

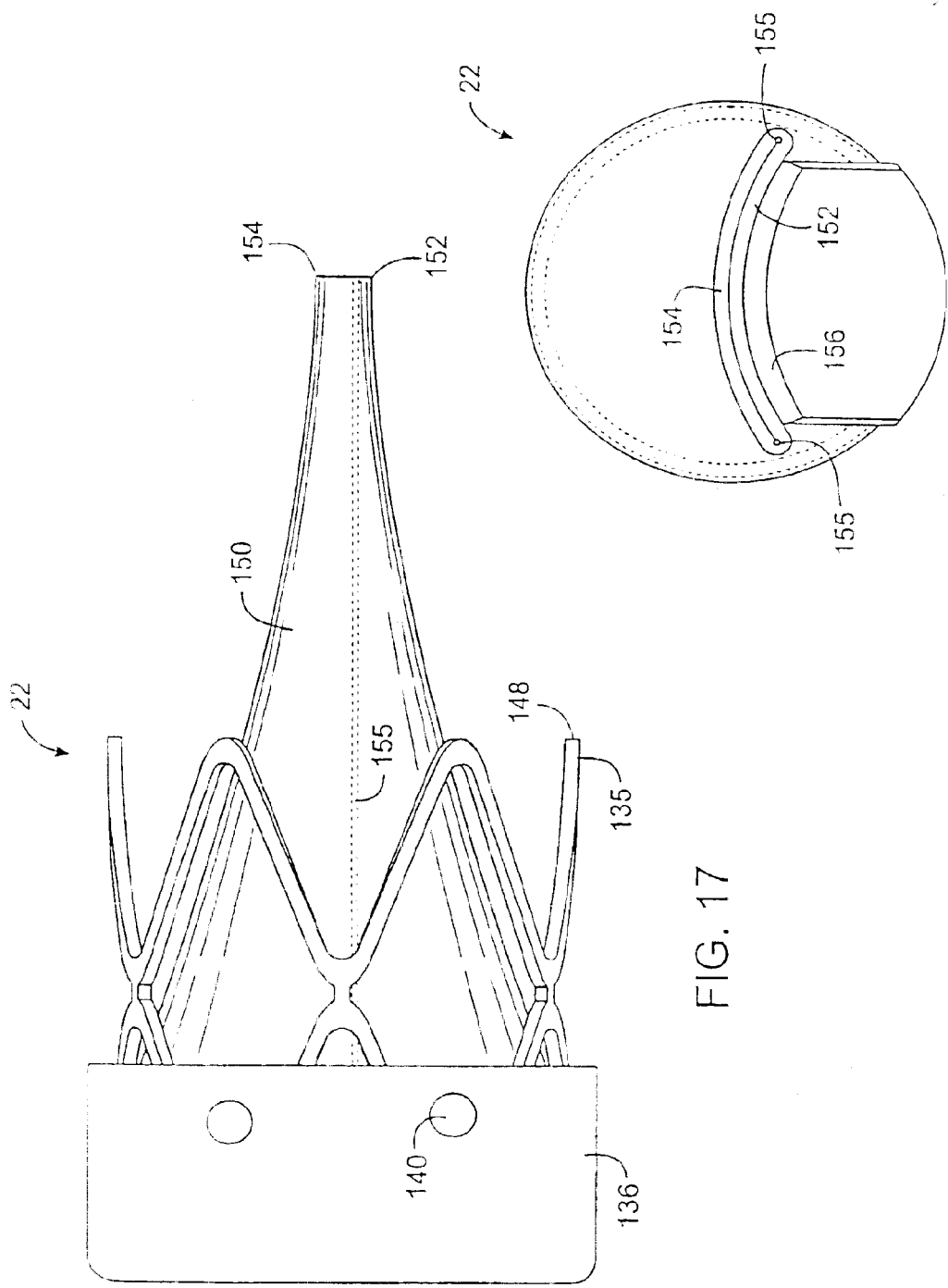

METHODS AND DEVICES FOR USE IN PERFORMING PULMONARY PROCEDURES

CROSS-REFERENCE TO RELATED APPLICATIONS

This application is a continuation of U.S. patent application Ser. No. 09/797,910, filed Mar. 2, 2001 entitled "Methods and Devices for use in Performing Pulmonary Procedures" by Deem et al., which is a continuation-in-part of U.S. patent application Ser. No. 09/519,735 filed Mar. 4, 2000 entitled "Methods and Devices for use in Performing Pulmonary Procedures" by Deem et al., the full disclosures of which are incorporated herein by reference.

BACKGROUND

1. Field of the Invention

The present invention relates generally to methods and devices for use in performing pulmonary procedures, and more particularly, procedures for treating various diseases of the lungs.

2. Description of the Related Art

Pulmonary diseases such as emphysema and chronic obstructive pulmonary disease (COPD) reduce the ability of one or both lungs to fully expel air during the exhalation phase of the breathing cycle. The diseased lung tissue is less elastic than healthy lung tissue, which is one factor that prevents full exhalation of air. During breathing, the diseased portion of the lung does not fully recoil due to the tissue being less elastic. Consequently, the diseased (e.g., emphysematic) lung tissue exerts a relatively low driving force, which results in the diseased lung expelling less air volume than a healthy lung. The reduced air volume exerts less force on the airway which allows the airway to close before all air has been expelled, another factor that prevents full exhalation.

The problem is further compounded by the diseased, less elastic tissue that surrounds the very narrow airways that lead to the alveoli (the air sacs where oxygen-carbon dioxide exchange occurs). This tissue has les tone than healthy tissue and is typically unable to maintain the narrow airways open until the end of the exhalation cycle. This traps air in the lungs and exacerbates the already-inefficient breathing cycle. The trapped air causes the tissue to become hyper-expanded and no longer able to effect efficient oxygen-carbon dioxide exchange. Applying suction to these narrow airways (a procedure proposed in the literature for deflating the diseased portion of the lung) may collapse the airways due to the surrounding diseased tissue, thereby preventing successful fluid removal.

In addition, hyper-expanded lung tissue occupies more of the pleural space than healthy lung tissue. In most cases, a portion of the lung is diseased while the remaining part is healthy and therefore still able to efficiently carry out oxygen exchange. By taking up more of the pleural space, the hyper-expanded lung tissue reduces the amount of space available to accommodate the healthy, functioning lung tissue. As a result, the hyper-expanded lung tissue causes inefficient breathing due to its own reduced functionality and because it adversely affects the functionality of adjacent healthy tissue.

Lung reduction surgery is a conventional method of treating lung diseases such as emphysema. A diseased portion of the lung is surgically removed which makes more of the pleural space available to accommodate the functioning, healthy portion of the lung. The lung is typically accessed through a median sternotomy or small lateral thoracotomy. A portion of the lung, typically the upper lobe of each lung, is freed from the chest wall and then resected, e.g., by a stapler lined with bovine pericardium to reinforce the lung tissue adjacent the cut line and also to prevent air or blood leakage. The chest is then closed and tubes are inserted to remove air and fluid from the pleural cavity. The conventional surgical approach is relatively traumatic and invasive, and, like most surgical procedures, is not a viable option for all patients.

More recently proposed treatments include the use of devices that employ RF or laser energy to cut, shrink or fuse diseased lung tissue. Another lung volume reduction device utilizes a mechanical structure that is used to roll the lung tissue into a deflated, lower profile mass that is permanently maintained in a compressed condition. As for the type of procedure used, open surgical, minimally invasive and endobronchial approaches have all been proposed. Another proposed device (disclosed in publication no. WO 98/48706) is positioned at a location in the lung to block airflow and isolate a part of the lung. The publication states that the occlusion device is introduced through an endobronchial delivery device, and is resiliently deformable in order to provide a complete seal against airflow.

The search for new and better treatments underscores the drawbacks associated with existing pulmonary procedures. Accordingly, there is a need in the art for improved methods and devices for performing pulmonary procedures, and in particular, treating lung diseases such as emphysema.

SUMMARY

In one embodiment, there is disclosed a method for treating a patient's lung. The method includes steps of selecting a hollow structure in a patient's lung, the hollow structure defining a pathway for conducting fluid flow in at least first and second directions, and allowing fluid flow within the pathway in the first direction while controlling fluid flow in the second direction.

In another embodiment, there is disclosed a method for treating a patient's lung. This method includes steps of providing a valve which allows fluid flow in a first direction and limits fluid flow in a second direction, and positioning the valve at a desired location in a lung of a patient with the first direction corresponding to an exhalation direction and the second direction corresponding to an inhalation direction.

In another embodiment, there is disclosed a method for treating a patient's lung that includes steps of providing a flow control element that limits fluid flow in at least one direction, positioning the flow control element at a location in a lung of a patient with the one direction substantially corresponding to an inhalation direction, and removing the flow control element after a period of time.

In another embodiment, there is disclosed a method for treating a patient's lung, the method comprising steps of selecting a hollow structure in a patient's lung, the hollow structure defining a pathway for conducting fluid flow in at least first and second directions, applying suction to draw fluid through the pathway in the first direction, and substantially preventing fluid flow through the pathway in the second direction.

In another embodiment, there is disclosed a system for treating a patient's lung. The system includes a flow control element sized and configured to be positioned in a hollow structure located in a patient's lung, the flow control element including a valve member that permits fluid flow in a first direction while substantially preventing fluid flow in a second direction. A delivery device is sized and configured to be guided to and positioned in or adjacent the hollow structure, and the flow control element is removably mounted on the delivery device. This valve may be a poppet, ball, duckbill, heimlick, flat or leaflet valve.

In another embodiment, there is disclosed a system for treating a patient's lung. The system includes a measuring device for determining the approximate size of a hollow structure in a patient's lung, and a flow control element sized and configured to be positioned in a hollow structure located in a patient's lung, wherein the flow control element allows fluid flow in a first direction but substantially prevents fluid flow in a second direction.

In another embodiment, there is disclosed a system for treating a patient's lung. This system includes a flow control element sized and configured to be positioned in a hollow structure located in a patient's lung, wherein the flow control element allows fluid flow in a first direction but substantially prevents fluid flow in a second direction, and a removal device for removing the flow control element from the hollow structure subsequent to positioning the flow control element in the hollow structure.

In another embodiment, a blocking element is coupled to a delivery element. The blocking element is advanced to a location in a patient's lung. An expandable member is expanded to occlude a pulmonary passageway and air is then withdrawn from the lung. The blocking element is released to block air flow into the isolated portion of the lung. The blocking element may also be a valve. The expandable member may be carried by the delivery element or by a separate element.

In still another embodiment, a device is advanced through the blocking element after implantation of the blocking element. A procedure, such as delivery or evacuation of fluids or liquids, may then be performed with the device. The device is then removed with the blocking element again preventing air from passing in the inhalation direction. The blocking element may also be a valve which permits air flow in an expiratory direction.

BRIEF DESCRIPTION OF THE DRAWINGS

FIG. 3 is an enlarged elevation view, in section, of a, flow control element forming part of the system shown in FIG. 2, wherein the flow control element allows fluid flow in a first direction but blocks fluid flow in a second direction;

FIG. 4 is an enlarged elevation view, in section, of an alternative flow control element that allows fluid flow in a first direction but blocks fluid flow in a second direction;

FIG. 5 is an enlarged elevation view, in section, of another alternative flow control element;

FIG. 6 is an enlarged elevation view, in section, of still another alternative flow control element;

FIG. 7 is a perspective view of an introducer constructed according to another embodiment of the invention;

FIG. 8 is an enlarged perspective view of a portion of the introducer shown in FIG. 7;

FIG. 17 shows another flow control element.

FIG. 18 is an end view of the flow control element of FIG. 17.

DETAILED DESCRIPTION

The present invention provides methods and devices for performing pulmonary procedures, for example, treating various lung diseases such as emphysema and COPD. One preferred embodiment of the invention provides a flow control element that allows fluid flow in a first direction and controls fluid flow in a second direction. As used herein, fluid means gas, liquid, or a combination of a gas(es) and liquid(s). In addition, controlled fluid flow, as used herein, means that the flow is altered in some manner, i.e., the flow is not unimpeded in the second direction. The specific manner in which fluid flow is controlled in the second direction depends on the construction of the flow control element. The flow control element may, for example, completely block, substantially block, limit, meter or regulate fluid flow in the second direction by a valve or other suitable structure.

As an example, when positioned in a hollow structure in a patient's body, such as a bronchiole in one of the lungs, the flow control element is oriented to allow flow in the exhalation direction but prevent fluid flow in the inhalation direction. The flow control element has a valve member that opens during exhalation in order to deflate or decompress the isolated lung portion distal to the flow control element. This maintains the diseased tissue in a decompressed state which prevents further hyper-expansion of the tissue. The invention also permits slow decompression of the lung tissue over a short or extended period of time.

The invention thus may be used to prevent fluid being drawn into one or more portion of a patient's lung. According to another aspect of the invention, a portion of the lung may be deflated by applying gentle suction (via the flow control element) to the hyper-expanded tissue without collapsing the walls of the narrow airways surrounded by diseased tissue. The suction draws air, liquid, mucous, etc., out of the lung portion to evacuate the diseased tissue. It will be recognized that these and other aspects of the invention may be practiced independently or in conjunction with each other.

Figure 1:
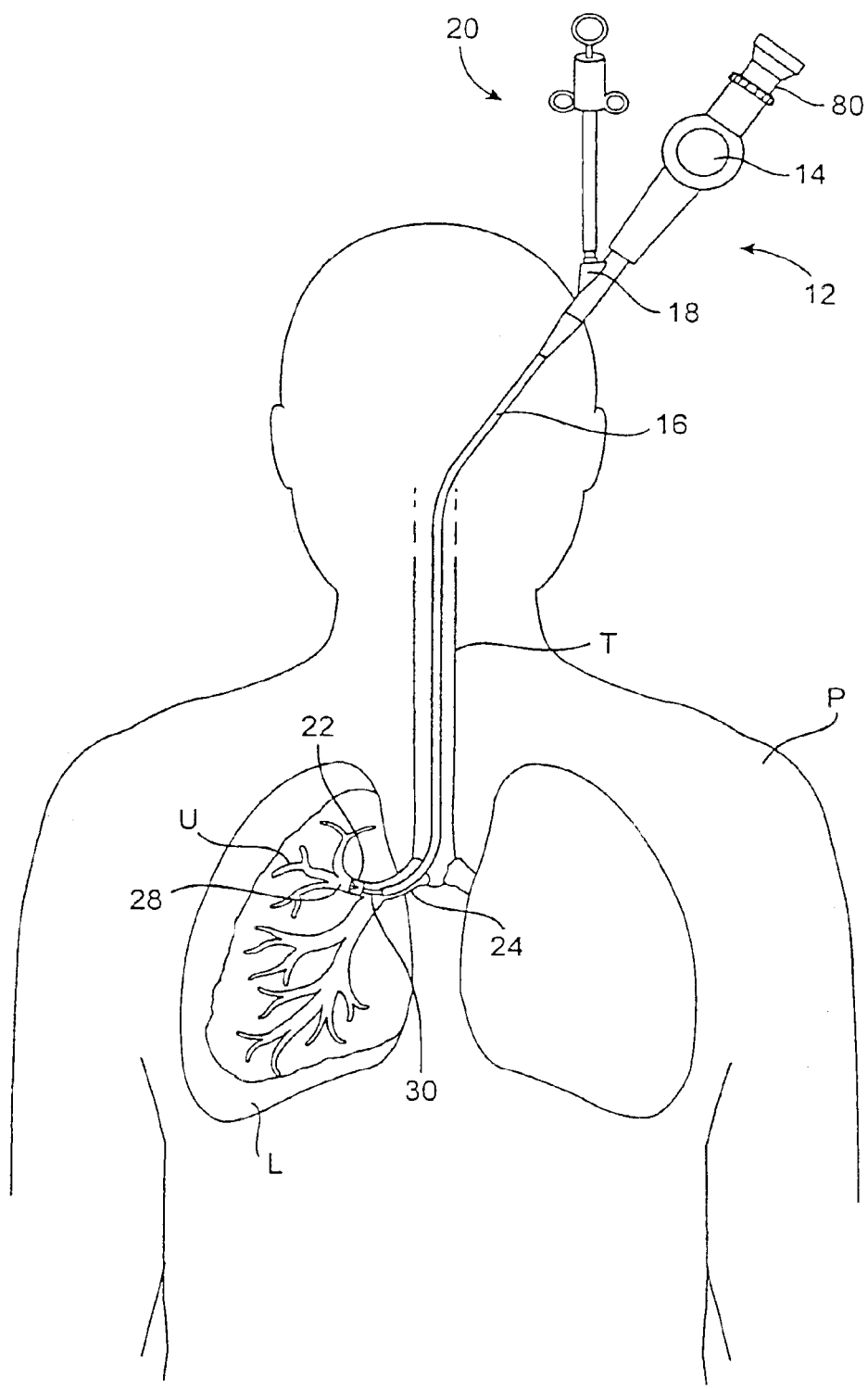
FIG. 1 is an elevation view schematically showing a system constructed according to one embodiment of the invention, the system being used to perform a pulmonary procedure on a patient.

FIG. 1 is a schematic view showing a system 10 constructed according to one embodiment of the invention for carrying out a pulmonary procedure on the lung L of a patient P. It should initially be noted that suitable systems, methods or devices outside of those specifically described herein may be used to practice the invention. As such, the system 10 is exemplary only and includes a bronchoscope 12 having a steering mechanism schematically indicated at 14, a shaft 16, and a port 18 which provides access to one or more working channels of the bronchoscope.

FIG. 1 shows a delivery device 20 constructed according to the invention. The delivery device 20 is shown positioned in the bronchoscope 12 in order to deliver a flow control element 22. The bronchoscope 12 has been passed into the patient's trachea T and guided into the right bronchus 24. The delivery device 20 is then manipulated with respect to the bronchoscope 12 via steering mechanism 14 to control placement of the flow control element 22. With reference to FIGS. 1 and 7–9, the delivery device 20 is movable within a bronchoscope working channel 26 (FIG. 8) and is guided into the desired location in the hollow structure, which in this case is a bronchiole 28. For purposes of explanation, the bronchiole 28 feeds an upper lobe U of the lung L which represents a diseased lung portion. The delivery device 20 is placed through the side port 18 and into the working channel 26, the distal end 30 of the delivery device 20 is moved out of the working channel, and the flow control element 22 is secured in position in the bronchiole 28.

Figure 2:
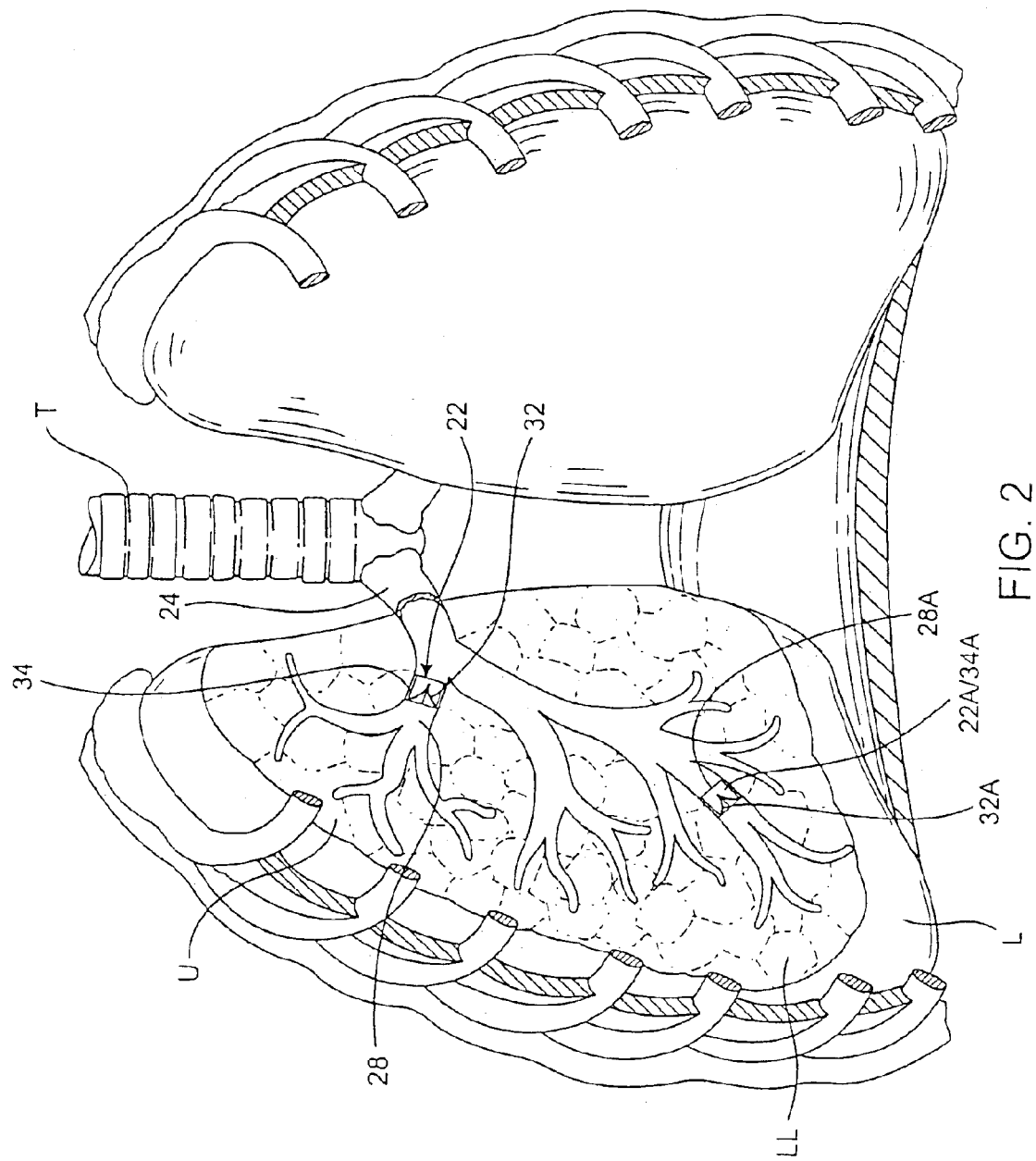
FIG. 2 is an enlarged elevation view of the lungs of the patient shown in FIG. 1 along with the system of the invention.

FIG. 2 is an enlarged view of the patient's lungs L shown in FIG. 1 after the introducer 12 and delivery device 20 have been removed, the flow control element 22 being left in the bronchiole 28. The flow control element 22, shown in more detail in FIG. 3, is in the form of a valve with a valve member 32 supported by a ring 34. It should be noted that FIG. 2 also illustrates a second flow control element 22A placed in a bronchiole 28A that feeds a lower lobe LL of the lung. The flow control element 22A includes a valve member 32A and a support ring 34A and reduces or prevents fluid from being inhaled into the hyper-expanded tissue of the lower lobe LL. It will be understood that any number of flow control elements may be used in a given procedure.

Referring to FIG. 3, which shows the flow control element 22 in detail, the valve member 32 is a duckbill-type valve and has two flaps defining an opening 36. The valve member 32 is shown in a flow-preventing orientation in FIG. 3 with the opening 36 closed. The valve member 32 is configured to allow fluid flow in a first direction (along arrow A) while controlling fluid flow in a second direction (along arrow B). In this embodiment, fluid flow in the direction of arrow B is controlled by being completely blocked by valve member 32. The first and second directions in which fluid flow is allowed and controlled, respectively, are preferably opposite or substantially opposite each other, for example, as shown in the Figures. It will be appreciated, though, that the invention may be practiced with the first and second directions different but not opposite each other.

As noted above, the valve member 32 of the flow control element 22 controls fluid flow by completely blocking such flow in the second direction. As such, the valve member 32 effectively functions as a one-way valve. Alternative embodiments of the invention utilize flow control elements that control fluid flow in the second direction without completely blocking such flow.

FIG. 4 shows an exemplary flow control element 38 constructed according to an alternative embodiment of the invention that limits, but does not block, fluid flow in at least one direction. The flow control element 38 comprises a valve member 40 supported by a ring 42. The valve member 40 is preferably a duckbill-type valve having a similar construction to that of the valve member 32, except that the flaps 44 are formed, secured, oriented or otherwise configured to maintain a flow opening 46 when in their flow-controlling (as opposed to flow-allowing) orientation. The opening 46 is sized and configured to achieve desired flow characteristics through the flow control element 38.

When the flow control element 38 is in its flow-allowing orientation (not shown), the flaps 44 spread apart and allow essentially unimpeded fluid flow out of the diseased lung portion. When the flow control element 38 is in its flow-controlling orientation, as shown in FIG. 4, the flaps move together to define opening 46 which allows a predetermined amount of fluid to be inhaled into the lung portion. This is in contrast to flow control element 22 which blocks fluid flow into the lung when in a flow-controlling orientation. It will of course be recognized that FIG. 4 shows only one way to achieve limited fluid flow in a given direction. The specific manner in which flow control is obtained may vary according to the invention, e.g., by varying the number, size, shape or position of the flow openings on the flow control element.

According to another aspect of the invention, the flow control element may be constructed to provide a pumping action that aids in moving gas or liquid within a hollow structure, such as a bronchiole. For instance, when the lung distorts during inhalation and/or exhalation, a mechanical pumping action is produced that may be used to move the gas or liquid to further deflate the isolated region of the lung. FIG. shows an exemplary flow control element 50 constructed according to this embodiment and including a pair of valve members 52, 54 supposed in series by a ring 56. The valve members 52, 54 each include a pair of flaps defining a valve opening (the valve members being shown in their closed, fluid flow blocking orientation in FIG. 5). A chamber 58 is defined between the valve members 52, 54 and produces a pumping effect on the fluid flowing through the flow control element 50. The chamber would collapse and expand with movement of the bronchiole (or other hollow structure in which it is inserted) to pump fluid from the diseased lung tissue.

The valve member 54 is coupled to a bellows 60 to enhance the pumping action and/or to control the amount of force needed to open the valve member. The wall 62 defining the chamber 58 is secured to the ring 56 so that the chamber 58 occupies the entire interior of the ring 56. The flow control element 50 may have a different configuration wherein the chamber 58 is defined by an air pocket located within the wall 62. This may prevent fluid collecting in the chamber 58. In addition, a power-driven pump may be used to draw fluid out of the lungs, e.g., a miniature batter-powered electric pump, or pumps that use physical or chemical characteristics, e.g., a change in air temperature, presence of an additional gas or liquid, change in pH, etc., to generate pumping force that evacuates air and mucous.

FIG. 6 shows yet another alternative flow control element 70 including a valve member 72 comprising a pair of flaps defining an opening, and ring 74 supporting the valve member 72. The valve member 72 is a duckbill-type valve that permits fluid flow in a first direction but prevents flow in a second direction. The ring 74 in this embodiment comprises a stent 76 having struts 78 to enhance fixation of the flow control element 70 in the hollow body structure (not shown). The valve member 72 may be attached to the stent 76 by any suitable means, e.g., molded to the stent, suture, fasteners, adhesives, etc. The stent 76 is movable between collapsed and expanded (FIG. 6) orientations to enable easy delivery and deployment. That is, the flow control element 70 including stent 76 may be collapsed and held in a sheath for delivery through a relatively small space, for example, the working channel of a bronchoscope. (A typical bronchoscope has a diameter of about 6 or 7 mm, while the working channel has a diameter of about 2 or 3 mm.) Utilizing a collapsible flow control element may also be useful in introducing the flow control element through an small opening formed in the patient's thorax.

FIGS. 7 and 8 show in detail the bronchoscope 12 and the flow control element delivery device 20 described above in connection with FIG. 1. The bronchoscope 12 has an eyepiece 80 which is used to visualize the trachea and the various pathways of the lung during deployment of the flow control element 22. The bronchoscope 12 may be provided with a camera/recorder, an aspiration/irrigation system, or other auxiliary features. The steering mechanism 14 may comprise cables that move the distal tip of the bronchoscope shaft 16 over a desired angular range, for example, 0° through 180°. FIG. 8 shows the distal portion 30 of the bronchoscope 12 including the working channel 26 (which communicates with the side port 18), one or more fiber optic light guides 81, and a lens 82 for transmitting images to the eyepiece 80.

Figure 9:
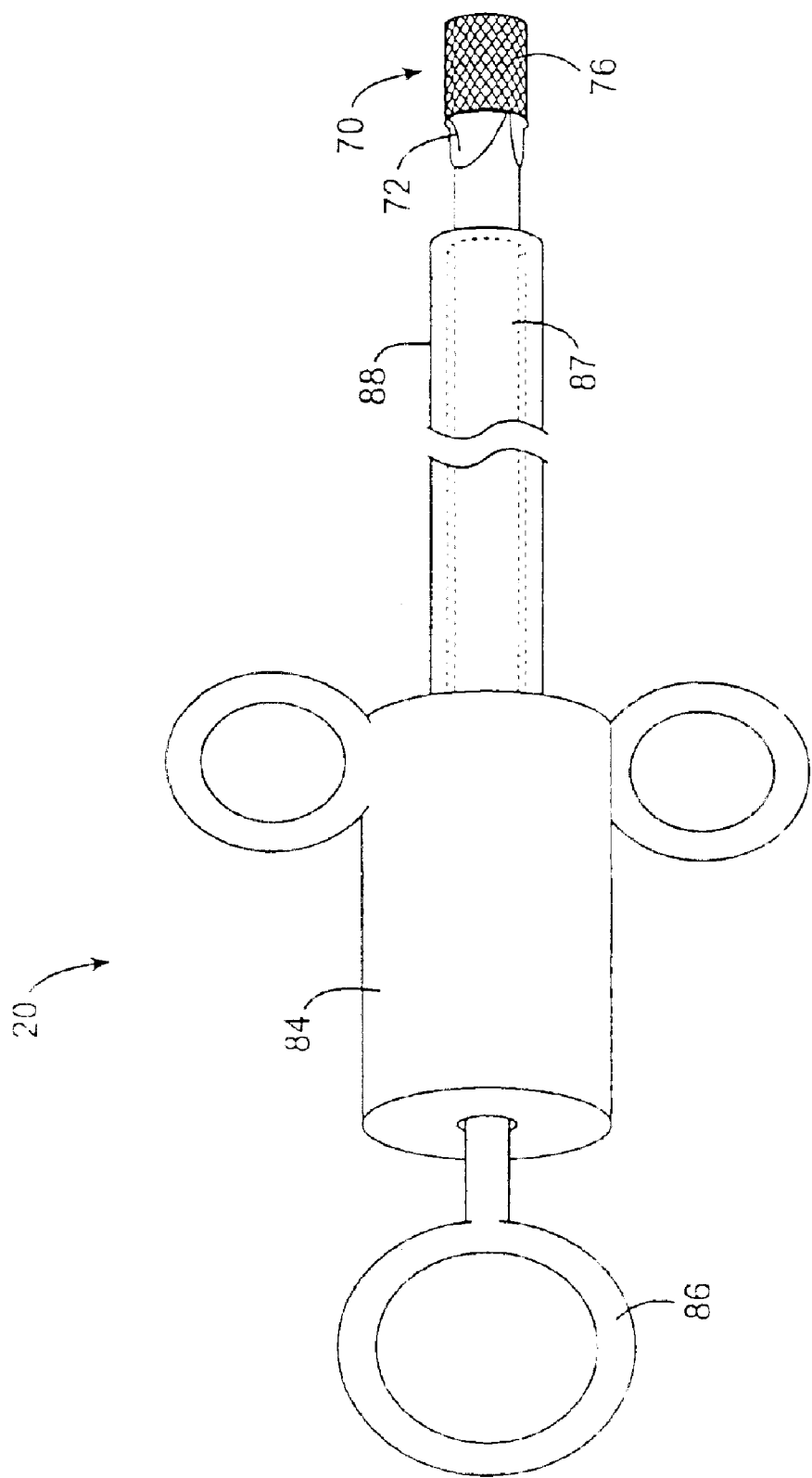
FIG. 9 is a perspective view of a delivery device constructed according to another embodiment of the invention for delivering a flow control element to a selected location in a patient's lung.

FIG. 9 shows the delivery device 20 to include a handle 84, an actuator 86, a support shaft 87 and a sheath 88. For purposes of illustration, the delivery device 20 will be described in connection with delivering the flow control element 70 of FIG. 6, although it will be understood that it may be used to deliver alternative flow control elements. The flow control element 70, and in particular the stent 76, is collapsed to a low profile orientation and then mounted on the shaft 87. The sheath 88 is moved distally from the position shown in FIG. 9 until it covers the stent body 76 (and the valve member 72, if desired) to maintain the flow control element 70 collapsed. (This position of the sheath is omitted for clarity.) The shaft 87 and sheath 88 are then passed into the side port 18 and working channel 26 of the bronchoscope 12 and guided to a desired location in the lung. The actuator 86 is used to remove the sheath 88 from the flow control element 70 which allows the stent 76 to expand. Stent 76 is preferably formed of a self-expanding material, e.g., Nitinol. In this case the flow control element 70 immediately expands and engages the tissue upon retraction of sheath 88. Alternatively, the stents could rely on a mechanism such as a balloon or heat activation to expand in use.

The flow control element of the invention may be guided to and positioned at a desired location in the pulmonary system, such as the bronchiole 28 shown in FIGS. 1 and 2, by various delivery devices or systems. For example, guidewire-based systems, introducer sheaths, cannulae or catheters, etc., may be used to deliver the treatment element in a minimally invasive manner. The above-described method for using a bronchoscope to introduce the flow control element may be modified by placing an introducer sheath over the bronchoscope. The sheath provides access should the bronchoscope need to be removed from patient's body, for example, in order to place a different size flow control element.

Figure 10:
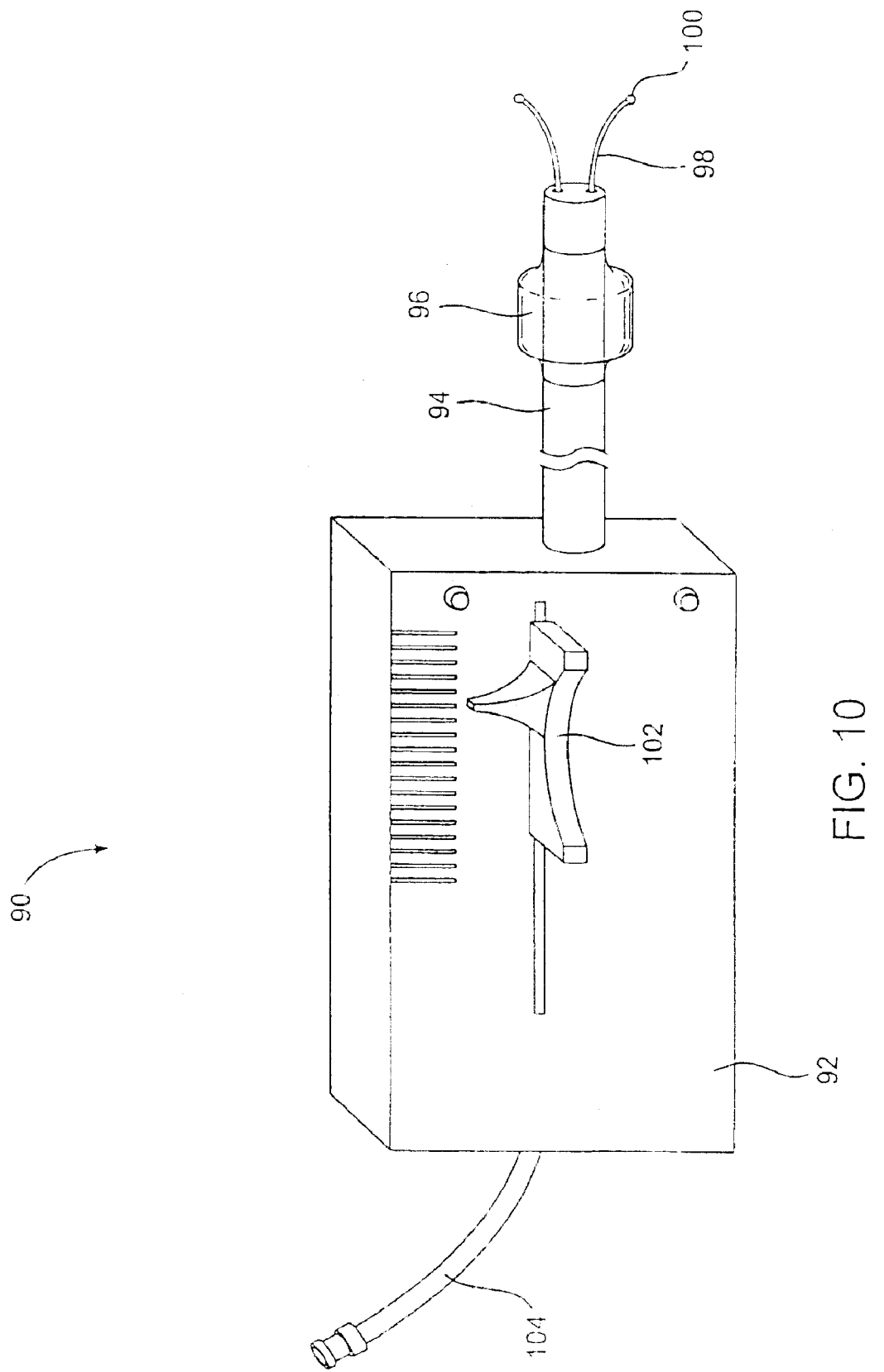
FIG. 10 is a perspective view of a measuring device constructed according to another embodiment of the invention for determining the size of a hollow structure prior to disposing a flow control element in the structure.

The invention is preferably carried out by first determining the approximate size of the target lumen, i.e., the hollow structure in which the flow control element will be placed. FIG. 10 shows somewhat schematically an exemplary device for determining the size of a hollow structure in a patient's body, for example, a bronchiole in a lung. The device 90 includes a housing 92, shaft 94, positioning element, 96 and measuring elements 98. The measuring elements 98 have tips 100 that are moved into contact with the wall of the hollow structure, such as the inner surface of a bronchiole (not shown). The device 90 is calibrated so that when tips 100 of measuring elements 98 engage the wall of the bronchiole the indicator 102 displays the approximate size of the bronchiole. An electrical coupling 104 powers the device 90.

The positioning element 96 is optional and may be used to fix the position of the measuring elements 98 within the bronchiole so as to obtain more precise measurement. The illustrated element 96 is an inflatable balloon, although other elements could be used to center and hold the shaft 96 within the bronchiole. Any suitable means may be used for ensuring that the measuring elements 98 do in fact contact the bronchiole wall in order to provide a true reading. The measuring elements 98 may be moved distally (to the right in FIG. 10) until a visual indicator indicates that the tips 100 are in contact with tissue. Alternatively, a change in electrical resistance may be used to confirm contact between the measuring elements 98 and tissue. It should be noted that the device 90 is merely representative of the various means that may be used to determine the size of a hollow body structure.

In use, the shaft 94 of the measuring device 90 is passed through the bronchoscope working channel 26 and delivered to the site. The device 90 is then operated as described above to determine the approximate size of the bronchiole. The degree of precision with which the size of the hollow structure is measured will depend on the procedure being performed and user preference. After determining the size of the bronchiole the device 90 is removed from working channel 26, and delivery device 20 is inserted into the channel to deploy the flow control element in the bronchiole.

It may in some instances be necessary or desirable to remove a flow control element from a hollow structure in which it has been deployed. As an example, it may be the case that placement of a flow control element for a given period of time effects beneficial results on the diseased lung tissue. The time during which the diseased tissue is deflated and decompressed may allow the tissue to regain some elasticity as a result of being temporarily inactive. After the tissue has regained some or all of its elasticity, it would be better to remove the flow control element and allow the tissue to function efficiently. The flow control element, however, is preferably not removed before the tissue has a sufficient chance to recover.

Figure 11:
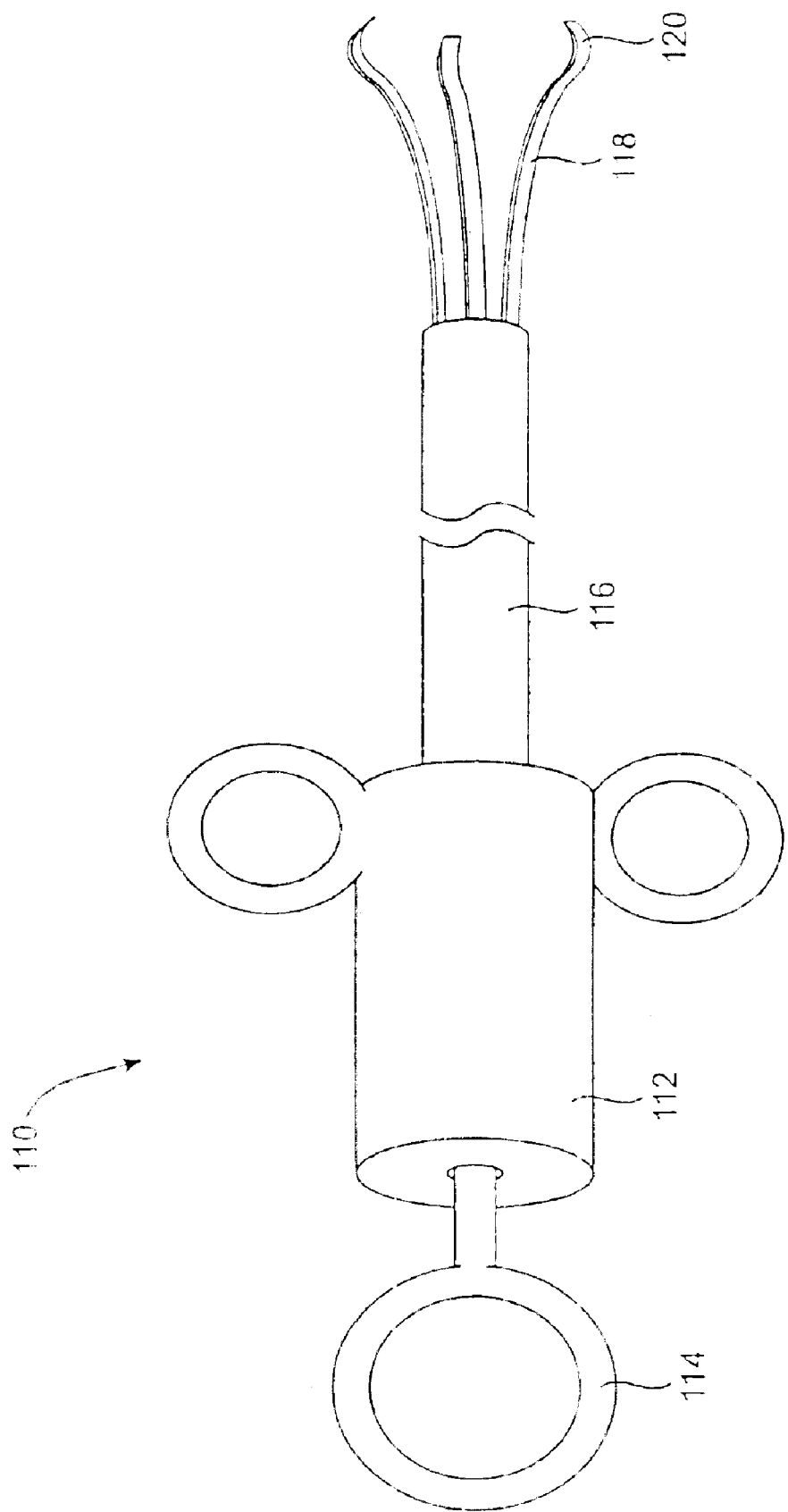
FIG. 11 is a perspective view of a removal device constructed according to another embodiment of the invention for removing a flow control element that has already been positioned in a hollow structure.
Figure 12:
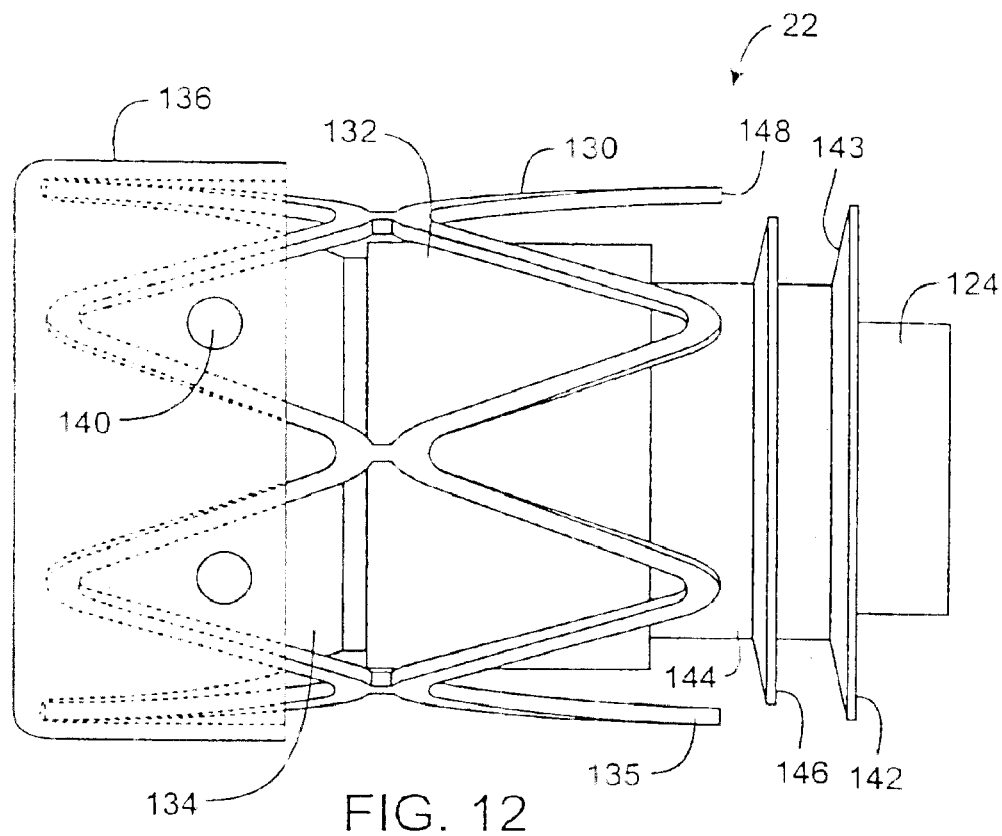
FIG. 12 is a side view of another flow control element.

Accordingly, the invention also provides methods and devices for removing a flow control element from a hollow structure such as a bronchiole in a patient's body. FIG. 11 shows a device 110 comprising a handle 112, an actuator 114, a shaft 116 and one or more removal components 118. The components 118 preferably have tips 120 configured to grasp a flow control element in order to remove the element from surrounding tissue. The shaft 116 of the device 110 is passed into a patient's trachea (not shown) and is guided to the previously-deployed flow control element; for example, the shaft 116 may be introduced through the working channel of a bronchoscope in the same manner as the delivery device 20. The removal components 118 are preferably collapsed within shaft 116 while the shaft is guided to the site. The components 118 are then extended into contact with the wall of the bronchiole. The tips 120 are used to grasp and remove the flow control element from the bronchiole.

The flow control element of the invention is secured in position in the hollow structure, such as bronchiole 28, so as to remain in place during breathing. The exterior of the flow control element may be configured along all or part of its exterior to aid in fixing the element in place, for instance, as schematically indicated by reference numeral 48 in FIGS. 3 and 4. The fixation structure 48 may comprise adhesives, tissue growth-inducing substances, fasteners, staples, clips, suture, stents, balloons, Dacron® sleeves, sintered, etched, roughened, barbed or alternatively treated surfaces, etc.

Placement of a flow control element constructed according to the invention in a patient's pulmonary system achieves several benefits. With reference to the illustrated flow control element 22, when deployed in the bronchiole 28 as shown in FIGS. 1 and 2, the element shows exhalation but prevents inhalation. The flow control element 22 thus limits or prevents the inhalation of additional fluid into the diseased lung portion. This is beneficial because it prevents further enlargement of the hyper-expanded tissue, which in turn maintains more room in the pleural space for healthy lung tissue. The flow control element 22 also allows any air being naturally exhaled by the patient (as well as any liquid, if present) to exit the lung, thereby deflating or compressing the tissue. The fluid is preferably permitted to flow unimpeded from the lung, but it may instead be metered or regulated in order to control deflation.

Figure 13:
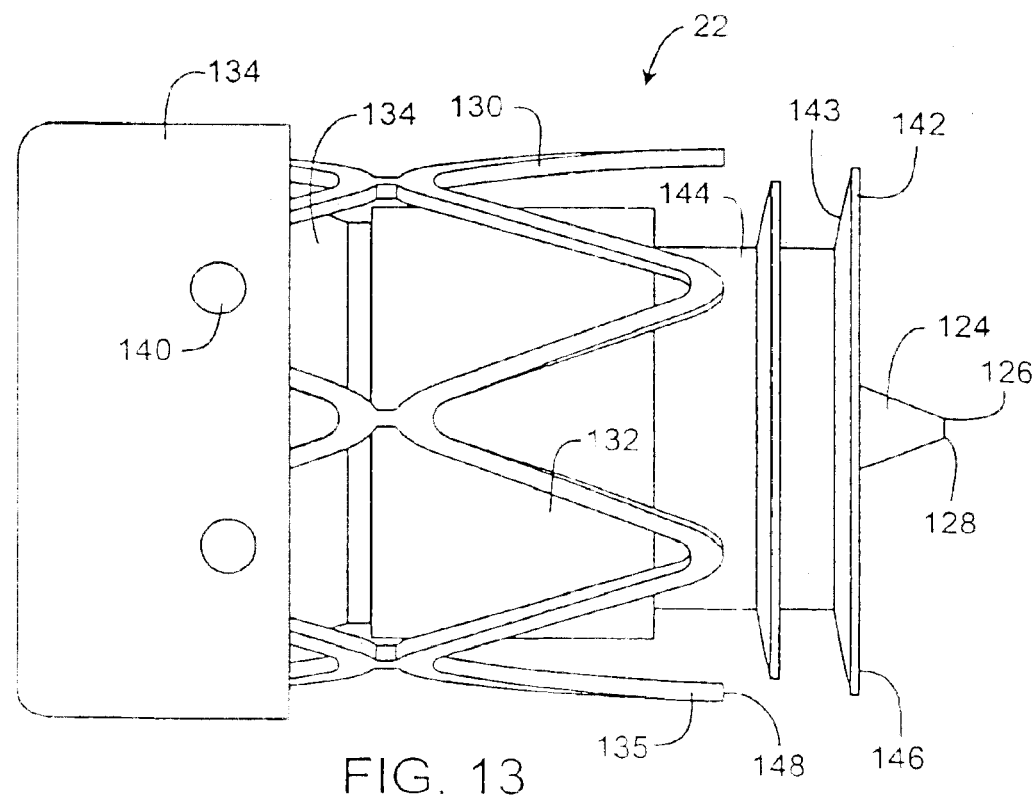
FIG. 13 is another side view of the flow control element of FIG. 12.
Figure 14:
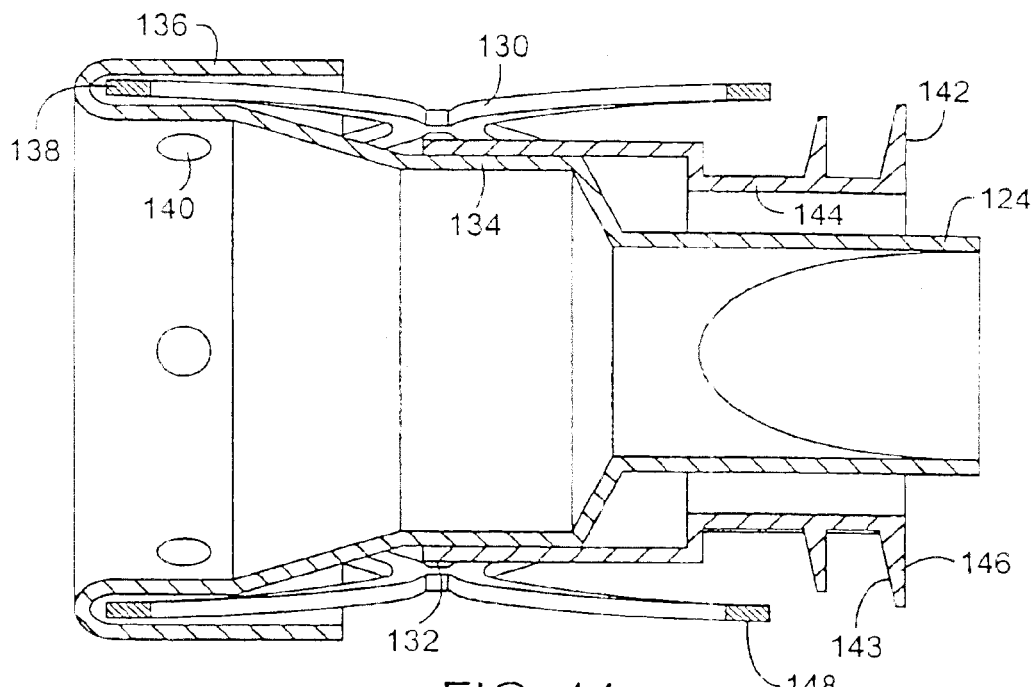
FIG. 14 is a cross-sectional view of the flow control element of FIG. 12.
Figure 15:
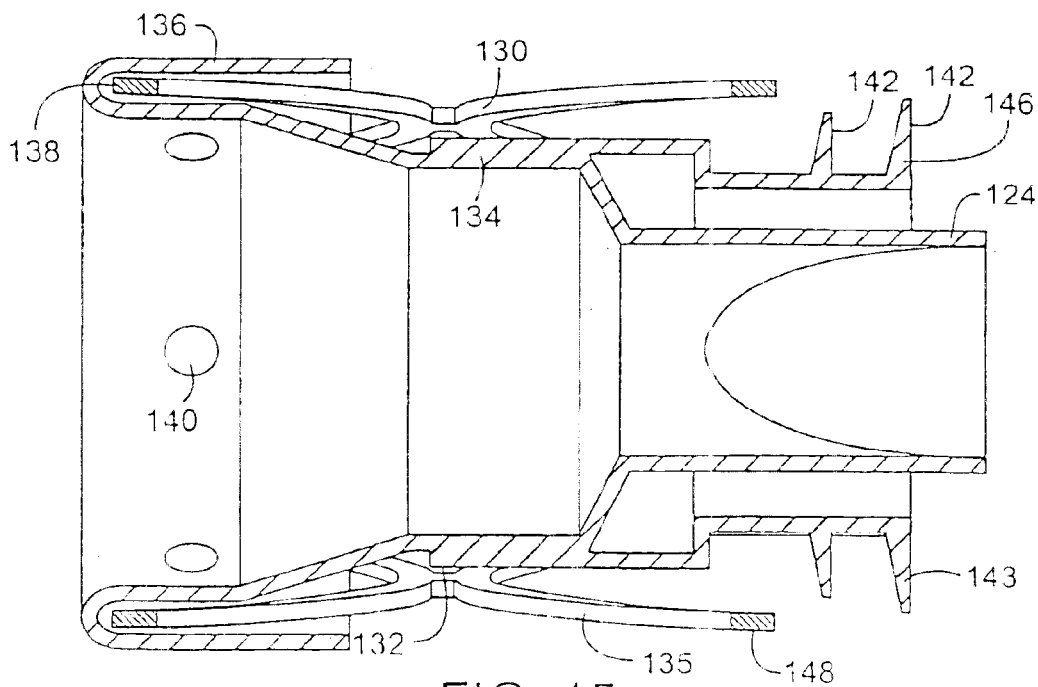
FIG. 15 is an alternative cross-sectional view of the flow control element of FIG. 12.
Figure 16:
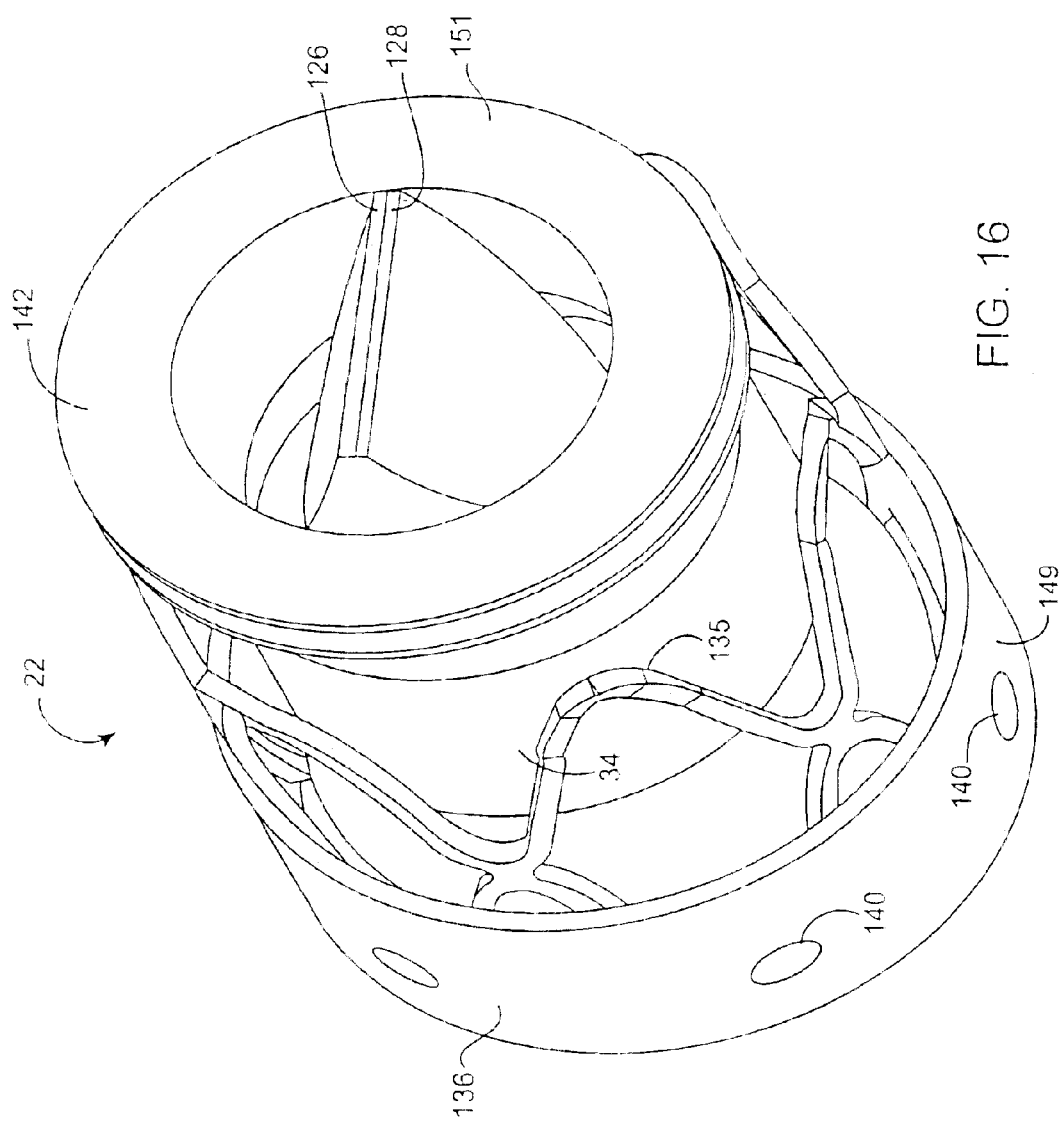
FIG. 16 is an isometric view of the flow control element of FIG. 12 altered to have a tapered shape.

Referring to FIGS. 12–16, another flow control element 22 is shown. The flow control element 22 serves as a blocking element which blocks air in the inhalation direction. The blocking element may also have a valve 124 which permits air flow in an exhalation direction but prevents air flow in the inhalation direction. The valve 124 may be any suitable valve such as any of the valves described herein. For example, FIGS. 13 and 16 show the valve 124 having a first lip 126 and a second lip 128 which engage one another in the closed position. The term valve as used herein may also refer to a check valve which permits flow in one direction but prevents flow in the other direction. Although the valves described herein are used with various aspects of the invention, other aspects of the invention may be practiced by blocking flow in both directions. For example, the devices and methods for accessing the isolated part of the lung may be used with devices which block air flow in both directions. Finally, flow in the exhalation direction may be regulated in another manner as described herein rather than simply with the valve.

The flow control element 22 has an expandable support structure 130. The support structure 130 is metallic and preferably a superelastic material such as Nitinol. The support structure 130 is formed by cutting, etching or otherwise removing material from a tube to form openings 132 as is generally known in the art of forming small, metallic tubes such as stents. Of course, the support structure 130 may be made in any other suitable manner and with other suitable materials. As an example, the support structure 130 may be a Nitinol tube which is laser cut to have six diamond-shaped openings 132.

The flow control element 22 has a body 134 coupled to the support structure 130. The body is preferably molded silicone or urethane but may be any other suitable material. The valve 124 is mounted to the body 134 and may be integrally formed with the body 134 as described below. The body 134 may be attached to the support structure 130 in any suitable manner. For example, the body 134 may be positioned in the support structure 130 and an end 136 averted over an end 138 of the support structure 130. The end 136 is attached to the rest of the body 134 through the openings 132 in the support structure 130 at connections 140 with an adhesive, adhesive rivet, heat weld or any other suitable method. An advantage of coupling the body 134 to the support structure 130 with the connections 140 is that the support structure 130 and body 134 may collapse and expand somewhat independently since the connections 140 are free to move in the openings 132.

The flow control element 22 may also have a sealing portion 142 which forms a seal with the wall of the pulmonary passage. The sealing portion 142 may be attached to the body 134 separately (FIG. 14) or may be integrally formed with the body 134 and valve 124 (FIG. 15). An advantage of the flow control element 22 is that a substantial portion of the element 22, such as the body 134 and valve 124, are integrally formed. In the embodiment of FIG. 15, the valve 124, valve body 134 and sealing portion 142 are all integrally formed. The sealing portion 142 extends around the valve 124 but is not coupled directly to the valve 124 so that the valve 124 is not subjected to forces exerted on or by the sealing portion 142. The sealing portion 142 extends from a tube 144 positioned around the valve 124.

The sealing portion 142 forms a ring 146 around the body 134. The ring 146 is made of a resilient, elastomeric material which improves sealing with the wall of the pulmonary passage. The ring 146 may have any suitable shape such as straight, tapered, angled or could have frustoconical surface 143 which angles the ring 146. The sealing portion 142 preferably forms two rings 146, and preferably three, which each have a different diameter to seal with different size passages. In this manner, the device may be used within a given size range. The ring 146 also may be designed to deflect to permit exhalation air to pass. During coughing, for example, the valve 124 will, of course, open to permit air to escape, however, the pressure force on the valve 124 can be reduced if the sealing portion 142 also opens to permit further venting of the isolated portion of the lung. As will be explained below, various other structures may also be used to provide valves which cooperate with the wall of the pulmonary passageway to permit venting of the isolated area.

The body 134 is coupled to the support structure 130 to provide an exposed part 135 of the support structure 130 which helps to anchor the device. The term exposed part shall mean a part of the support structure 130 not covered by the body 134. Of course, the exposed part 135 may be covered by another material so long as it is not covered by the body 134. The exposed part 135 of the support structure 130 may form anchoring elements 148 which anchor the support structure 130. The anchoring elements 148 are preferably v-shaped to improve anchoring. Of course, the anchoring elements 148 may also be barbs or the like. Referring to FIG. 16, the flow control device 22 may also be angled, tapered or flared so that one end 151 is larger than the other 149. Of course, any other shape, such as a cylinder or tube flared at both ends, may be used without departing from many aspects of the invention.

Referring to FIGS. 17 and 18, another flow control element 22 is shown wherein the same or similar reference numbers refer to the same or similar structure. The element 22 has a valve 150 which has first and second lips 152, 154 which engage one another in a closed position. The first lip 152 is preferably stiffer than the second lip 154 so that the first lip 152 biases the second lip 154 closed. The first lip 152 may be made stiffer than the second lip 154 in any manner such as by using a thicker layer of the same material, a stiffer material for the first lip, or by simply adhering or attaching a stiffener 156 to the first lip 152. The first and second lips 152, 154 are preferably formed by a tube of material with the stiffener 156 attached to one side to form the first lip 152. The first and second lips 152, 154 are also preferably curved as shown in FIG. 18. The element 22 is preferably made of molded silicone or urethane although any other suitable material may be used. The valve 150 also has reinforcing elements 155 at the lateral edges to further support the lips 152, 154. The valve 150 may, of course, have either the elements 155 or stiffener 156. Although the sealing portion 142 is not shown for clarity, the sealing portion 142 may also be provided.

Figure 19:
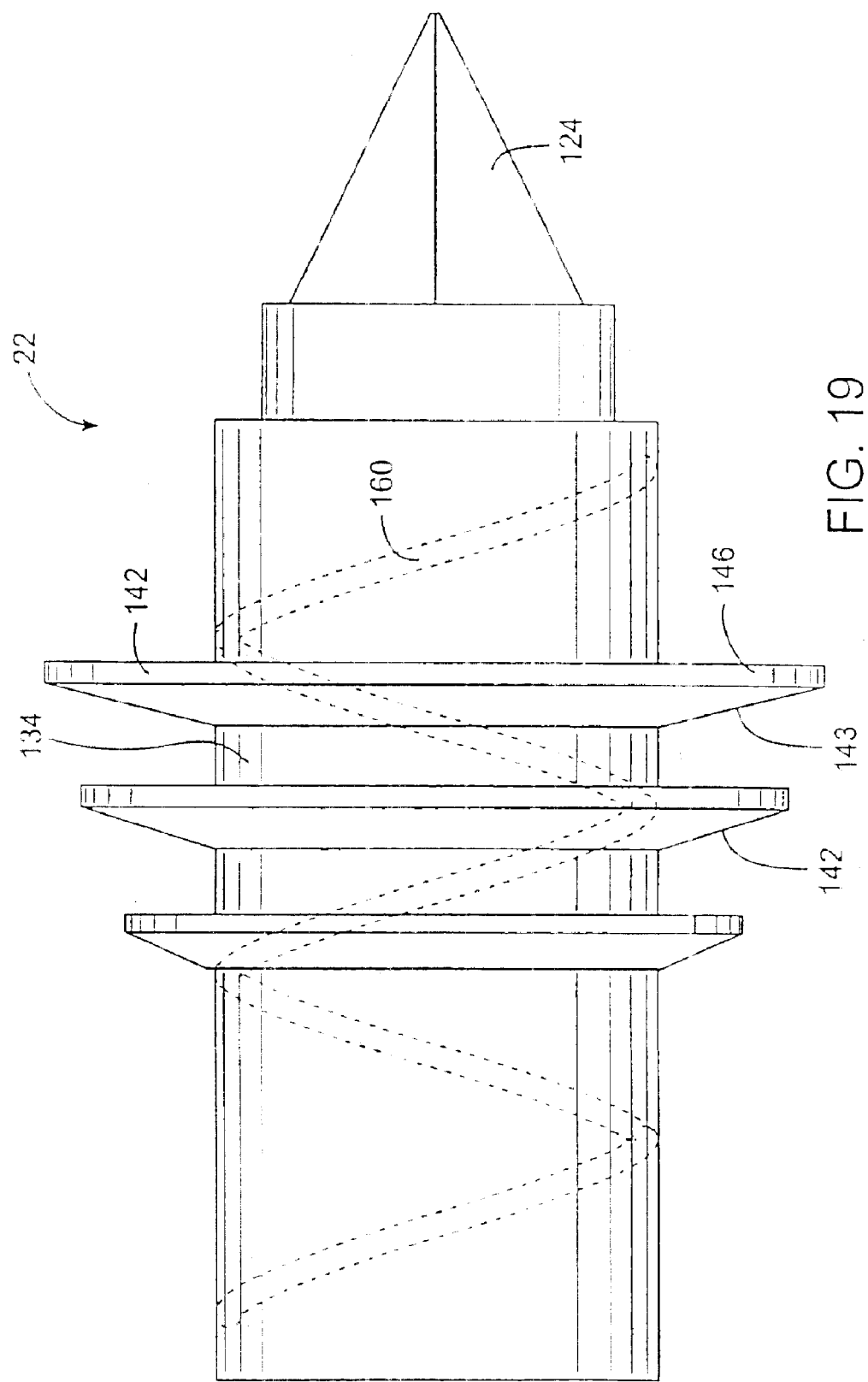
FIG. 19 shows another flow control element.

Referring to FIG. 19, another flow control element 22 is shown wherein the same or similar reference number show the same or similar structure. The flow control element 22 has the valve 124 and a number of sealing portions 142. The valve 124, sealing portion 142 and body 134 are integrally formed of a resilient material such as molded silicone or urethane. Of course, various other constructions may be used with the flow control element 22 without departing from the scope of the invention. The flow control element 22 may also have reinforcing element 158 such as a helical coil 160.

Figure 20:
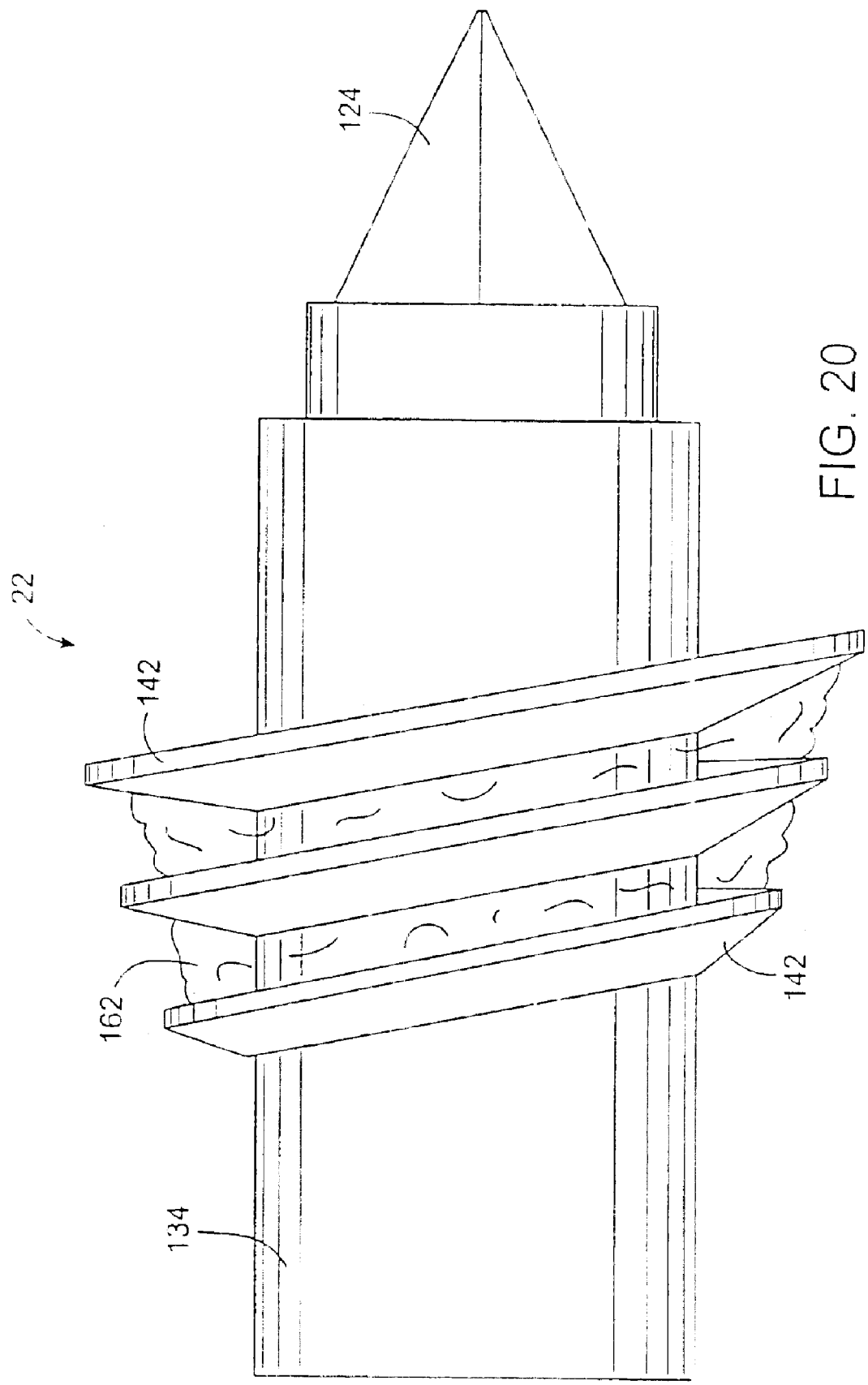
FIG. 20 shows still another flow control element.

Referring to FIG. 20, still another flow control element 22 is shown wherein the same or similar reference numbers refer to the same or similar structure. The flow control element 22 has a sealing portion 142 which has a helical shape. In one method of implanting the device, the element 22 is rotated so that the helical shape of the sealing portion 142 engages the wall to anchor the element 22.

Any of the flow control elements of the present invention may also be used with a sealant 162, such as an adhesive, which seals and/or anchors the device. Referring to FIG. 20, the sealant 162 is positioned on the exterior of the device is between the sealing portions 142. The sealant 162 is preferably a viscous substance which is applied to the exterior surface of the device before introduction. The sealant 162 may be an adhesive which also helps to anchor the device. The use of the sealant 162 may be used with any of the devices described herein.

Figure 21:
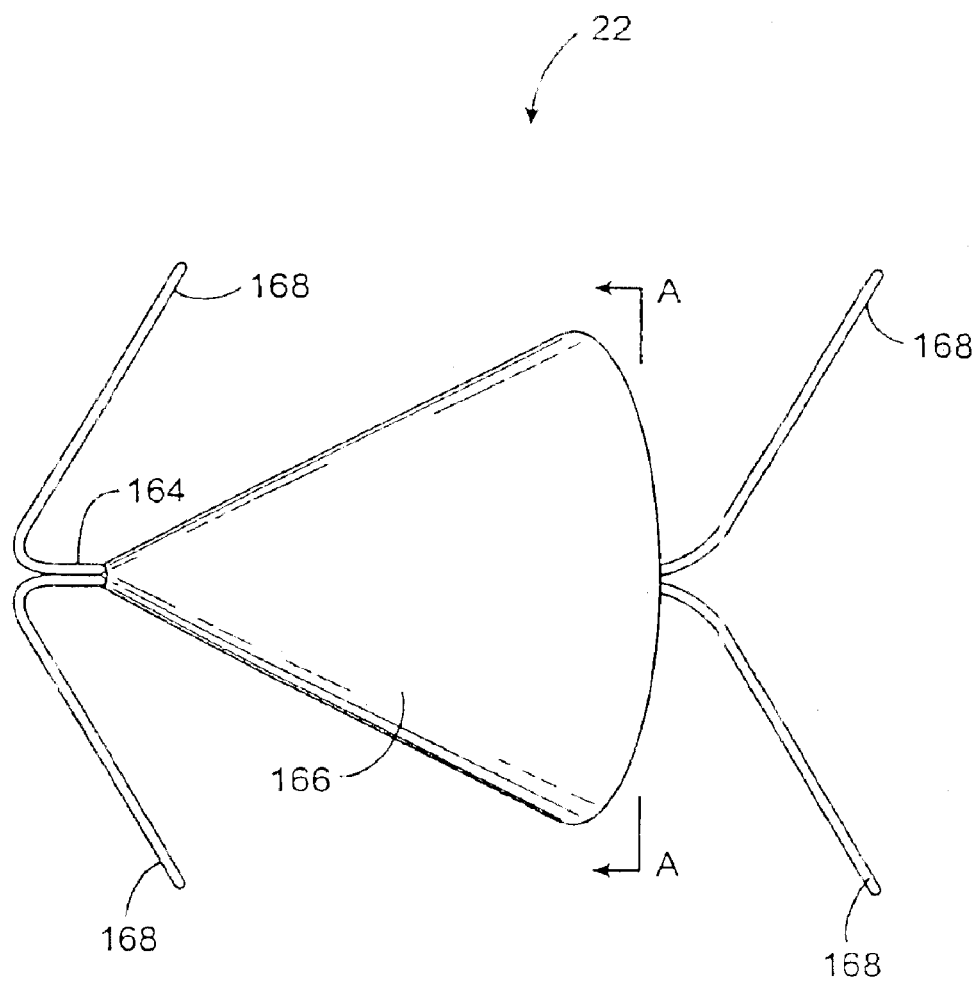
FIG. 21 is a side view of another flow control element.
Figure 22:
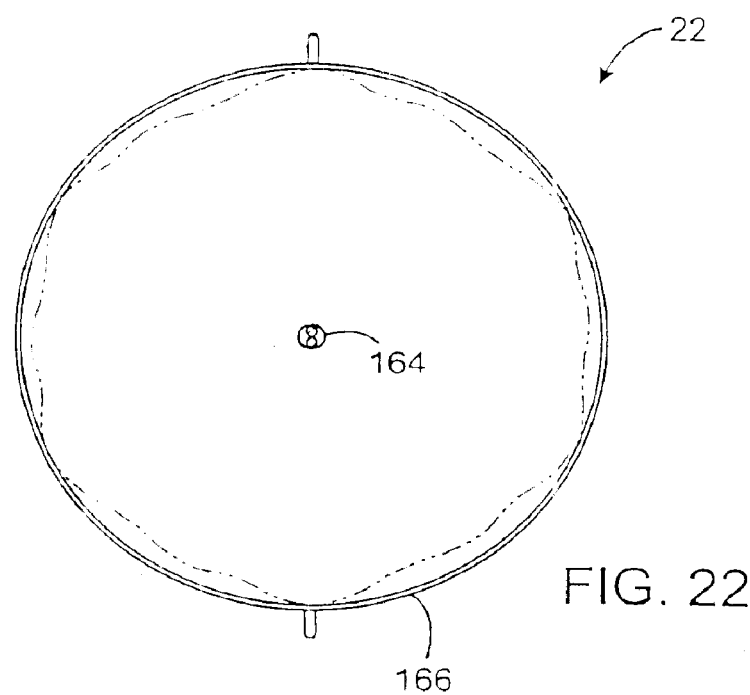
FIG. 22 is a cross-section of FIG. 21 along line A—A.
Figure 23:
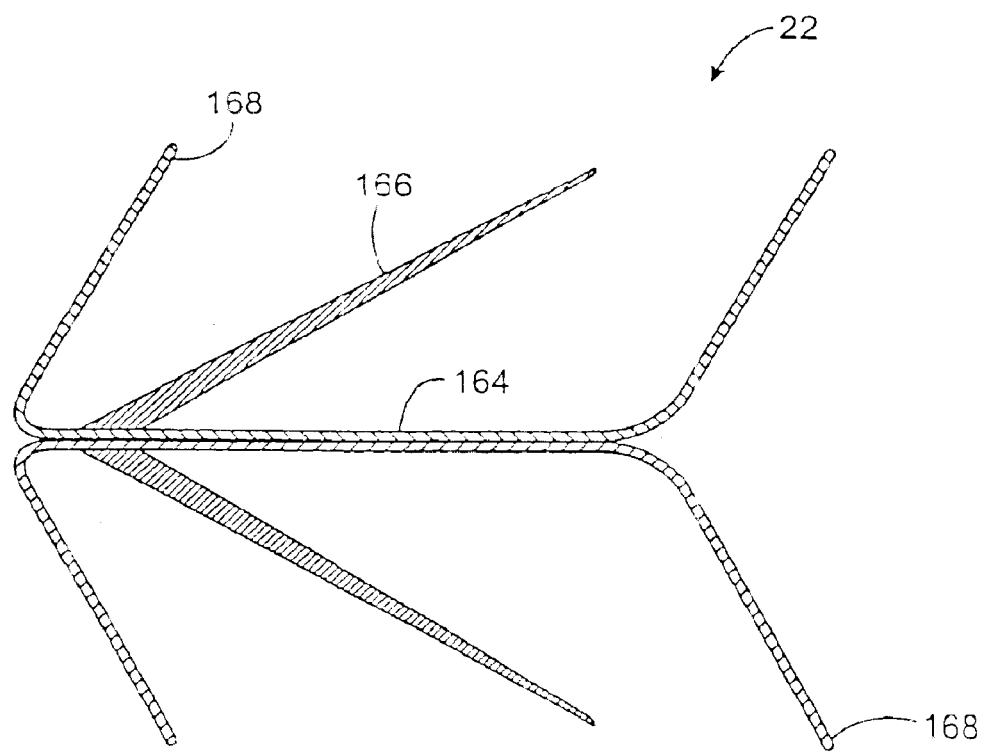
FIG. 23 is a longitudinal cross-section of FIG. 21.

Referring to FIGS. 21–23, still another flow control element 22 is shown wherein the same or similar reference numbers refer to the same or similar structure. The flow control element 22 has a support structure 164 which anchors a valve 166. The structure 164 has anchoring elements 168, preferably two, on each side of the valve 166. The anchoring elements 168 are formed by two wires attached together. Of course, any other suitable structure may be used for the structure 164 such as a stent-like structure or an expandable ring with barbs.

The valve 166 cooperates with the wall of the pulmonary passageway to vent the isolated area. The valve 166 is generally conical, however, any other shape may be used. The valve 166 may engage the pulmonary wall with a number of different configurations without departing from the scope of the invention, thus, the following preferred embodiments do not limit the scope of the invention. The valve 166 is elastic and yields to permit expiratory air to pass between the valve and the wall of the passageway. Referring to FIG. 22, the valve 166 is thinner near an end engaging the wall W so that the end of the valve 166 is more flexible.

Figure 24:
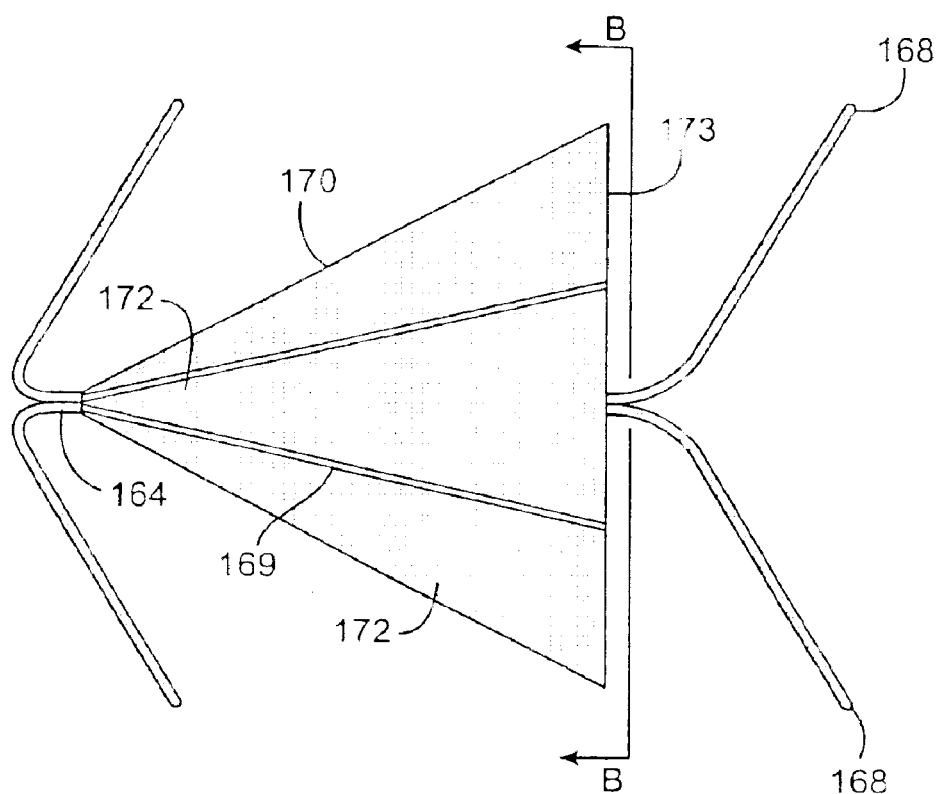
FIG. 24 is an alternative embodiment of the flow control device of FIG. 21.
Figure 25:
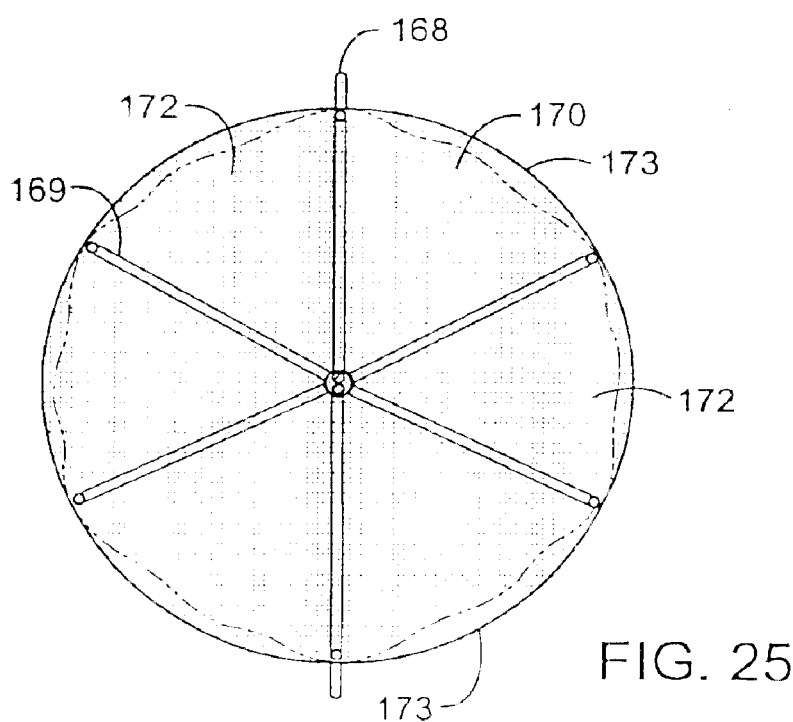
FIG. 25 is a cross-section of FIG. 24 along line B—B.

Referring to FIGS. 24 and 25, still another device is shown wherein the same or similar reference numbers refer to the same or similar structure. The device has a valve 170 with a number of sections 172 with each section 172 forming a seal with the wall of the pulmonary passage. The sections 172 are separated by wires 169 which provide a resilient structure. The device may be formed with any number of the sections 172 forming a valve structure 173 with the wall of the pulmonary passage.

Figure 26:
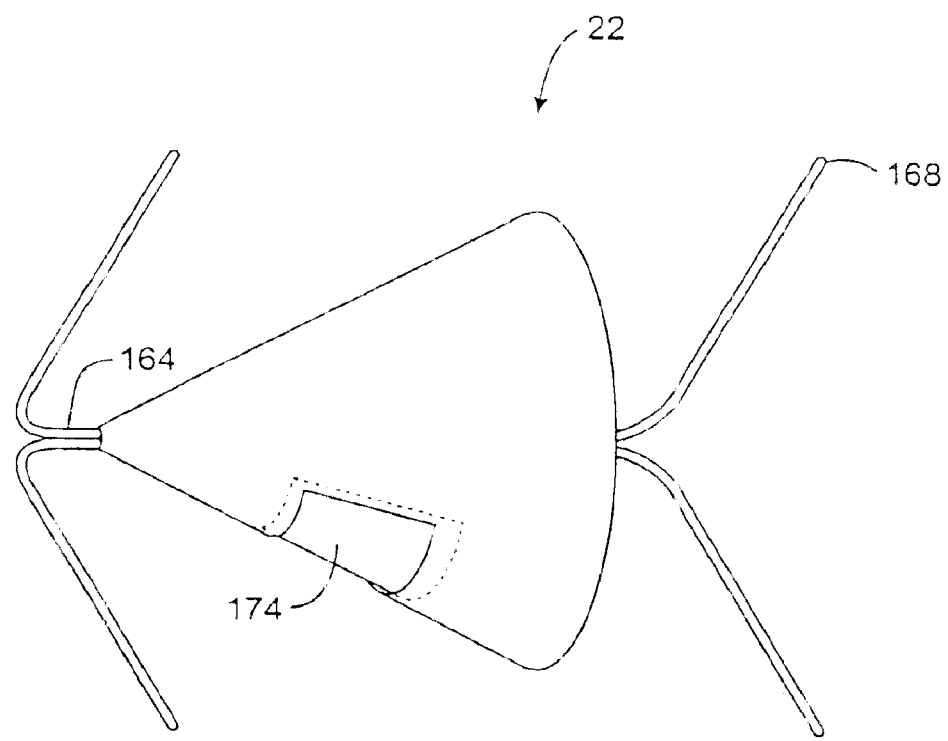
FIG. 26 shows another flow control element with a flap valve in a closed position.
Figure 27:
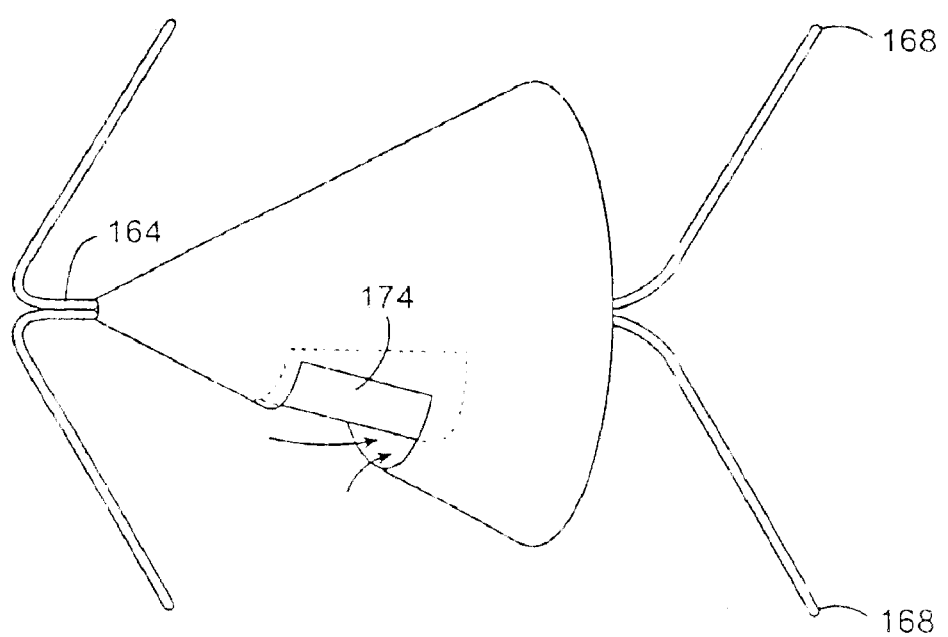
FIG. 27 shows the flap valve of FIG. 26 in an open position.

Referring to FIGS. 26 and 27, still another flow control element 22 is shown wherein the same or similar reference numbers refer to the same or similar structure. The element 22 has a flap valve 174 which opens to permit expiratory air to pass. The valve 174 is also generally conical. The term generally conical as used herein means that the cone may diverge from a cone in that the walls may be slightly curved, have a number of sections or a seam, flap or fold while still being generally cone-shaped.

Figure 28:
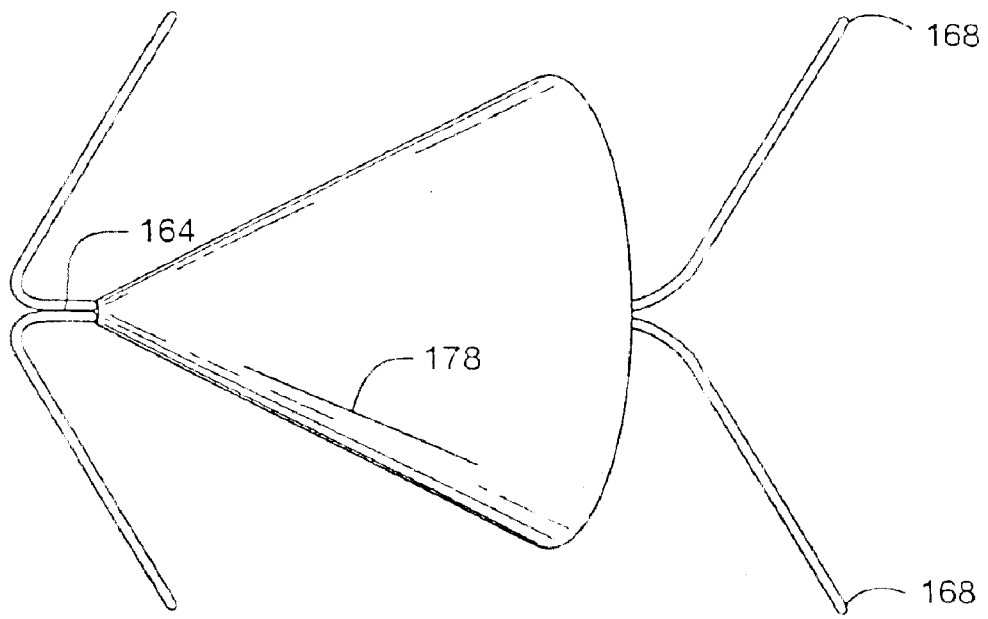
FIG. 28 shows a slit valve in a closed position.
Figure 29:
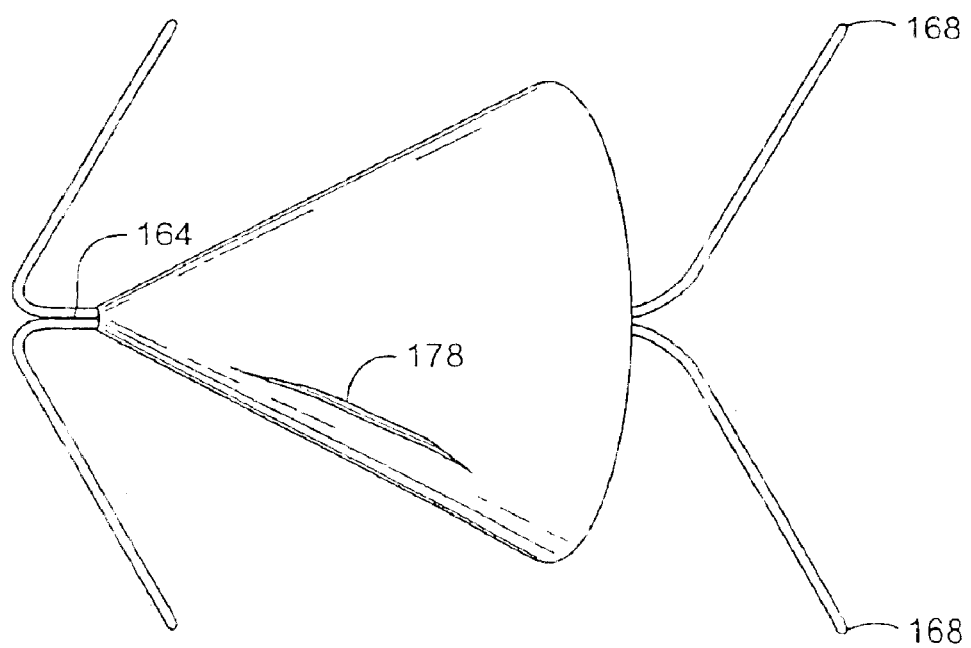
FIG. 29 shows the slit valve in an open position.

Referring to FIGS. 28 and 29, still another valve is shown having a slit or seam 178 which opens to permit expiratory air to pass. The slit or seam 178 may also be oriented and configured like a slit valve without departing from the scope of the invention.

Figure 30:
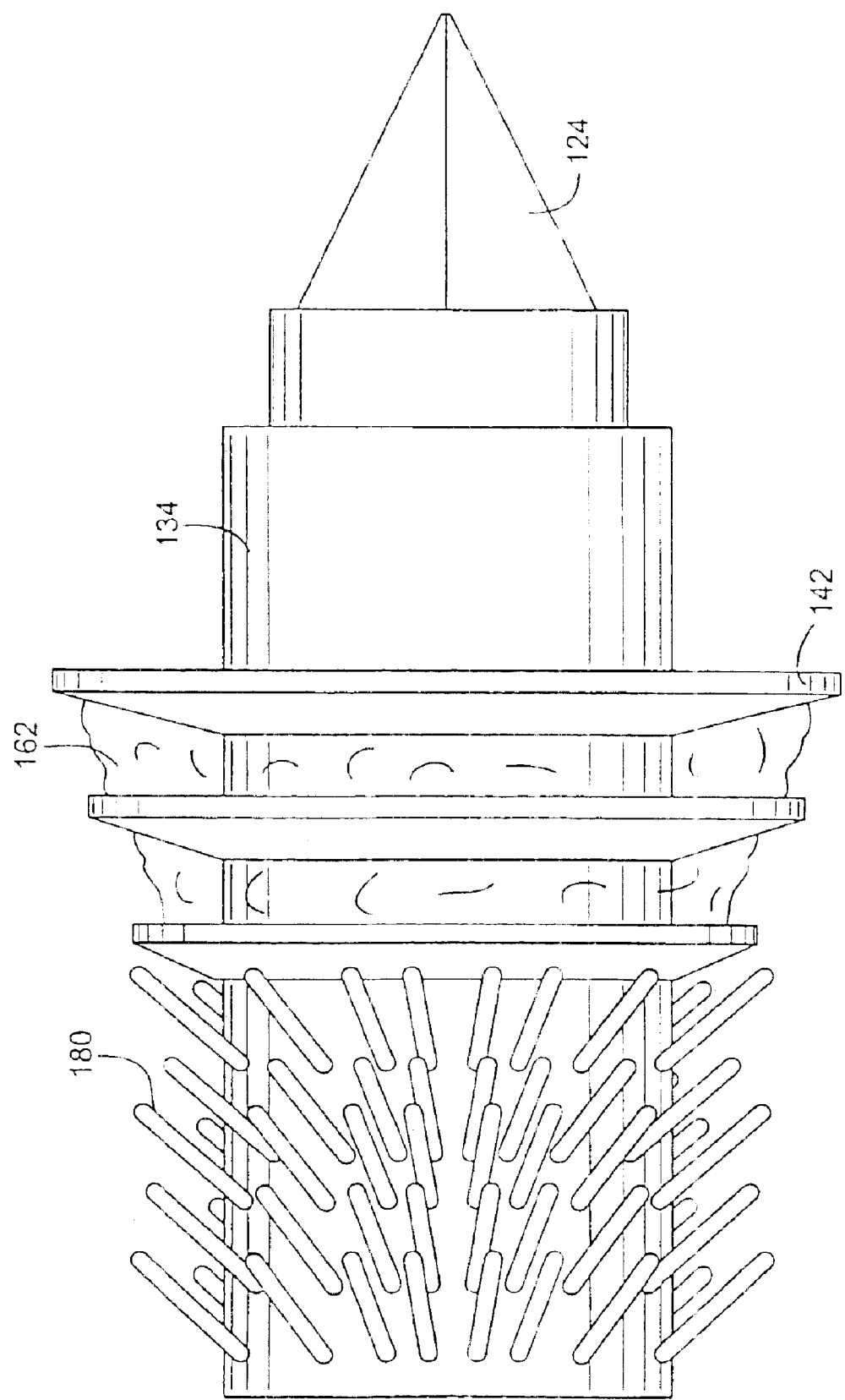
FIG. 30 shows a flow control element with bristles.

Referring to FIG. 30, still another flow control element 22 is shown in which the same or similar reference numbers refer to the same or similar structure. The device has the valve 124 but may have any other suitable valve. The device has flexible bristles 180, preferably more than 10, 20 or even 30 bristles 180, which anchor the device in the pulmonary passageway. The bristles 180 are preferably angled to resist forces in the expiratory direction so that pressure forces, such as forces developed during coughing, cannot dislodge the device. The bristles 180 may be used with the sealant 162 to provide an airtight seal.

Figure 31:
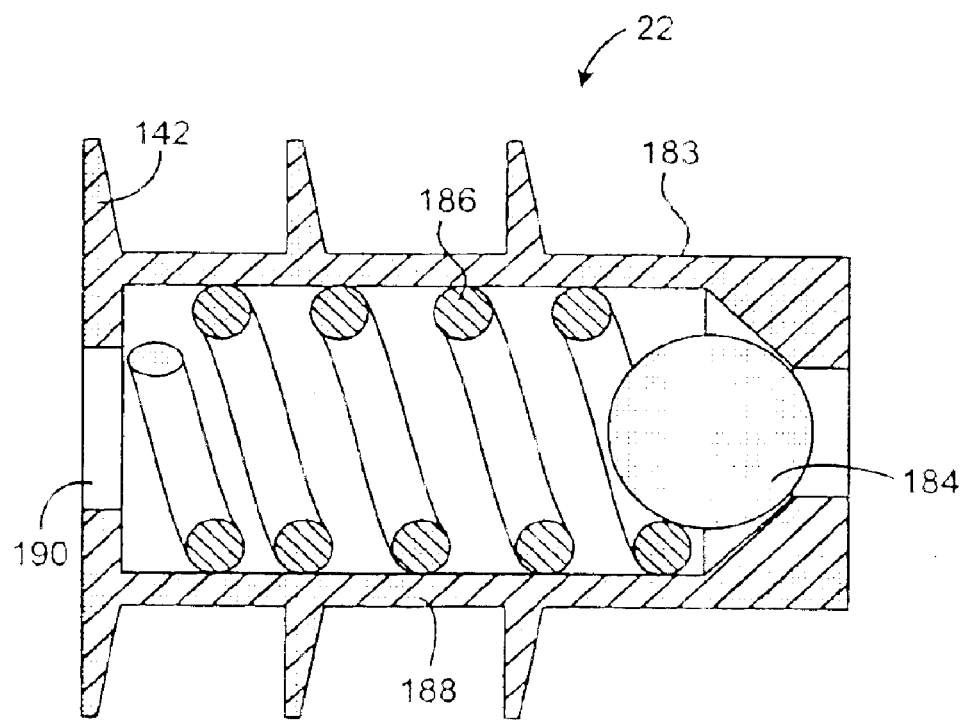
FIG. 31 is a cross-sectional view of a ball valve.
Figure 32:
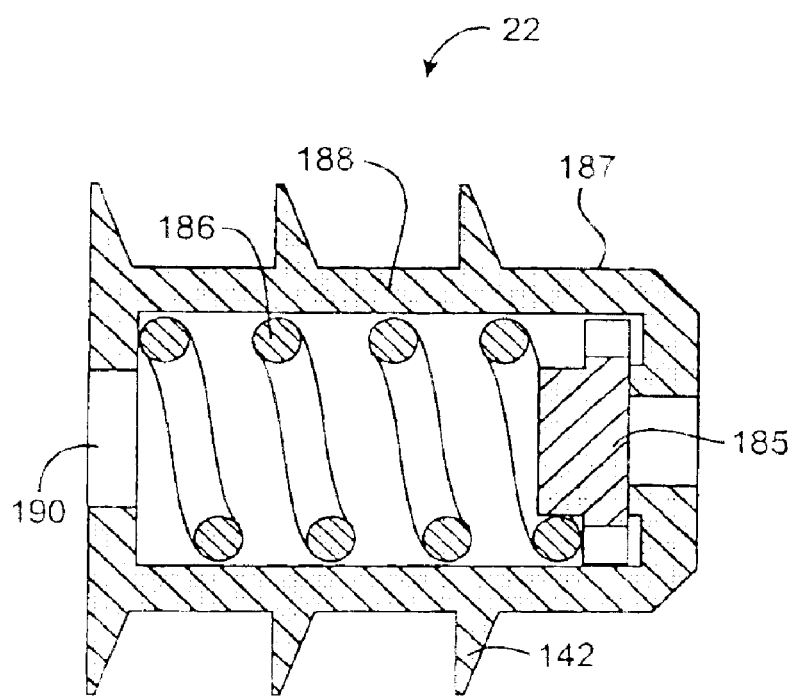
FIG. 32 is a cross-sectional view of a poppet valve.

Referring to FIG. 31, still another flow control element 22 is shown which includes a sealing element, such as a ball valve 184, biased toward the closed position to form a ball valve 183. The ball valve 184 is biased with a spring 186 although any other biasing element may be used. The device has a body 188 with the sealing portion 142. The body 188 has an opening 190 through which air may pass when the ball valve 184 opens. Referring to FIG. 32, still another device is shown which has a blocking element 185 rather than the ball valve 184 of FIG. 31 to form a poppet valve 187.

Figure 33:
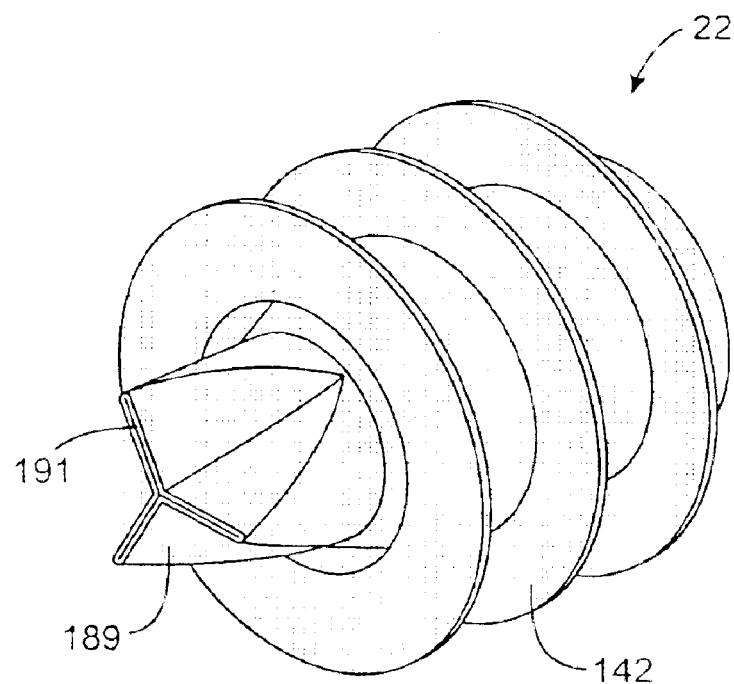
FIG. 33 shows a leaftlet valve.
Figure 34:
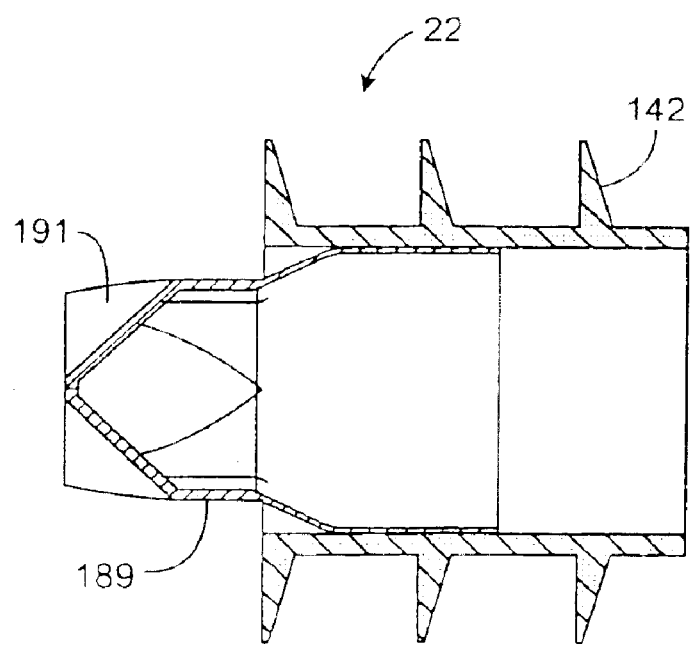
FIG. 34 is a cross-section of the leaflet valve of FIG. 33.
Figure 35:
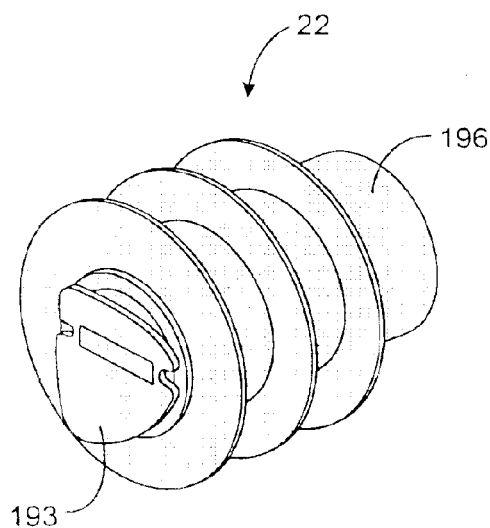
FIG. 35 shows another flap valve.
Figure 37:
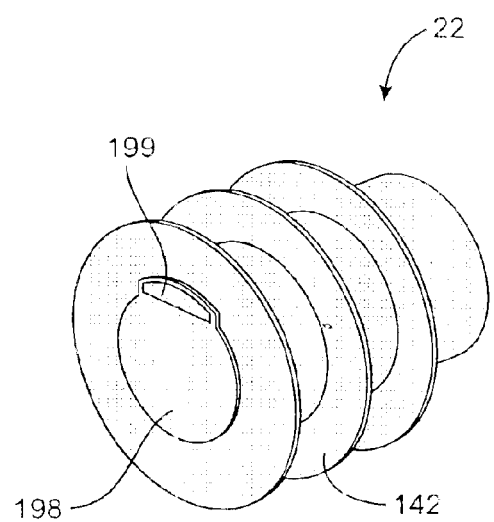
FIG. 37 shows still another flap valve.
Figure 36:
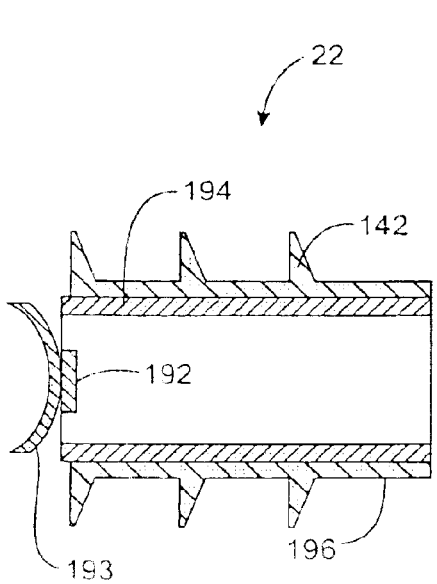
FIG. 36 is a cross-sectional view of the flap valve of FIG. 35.
Figure 38:
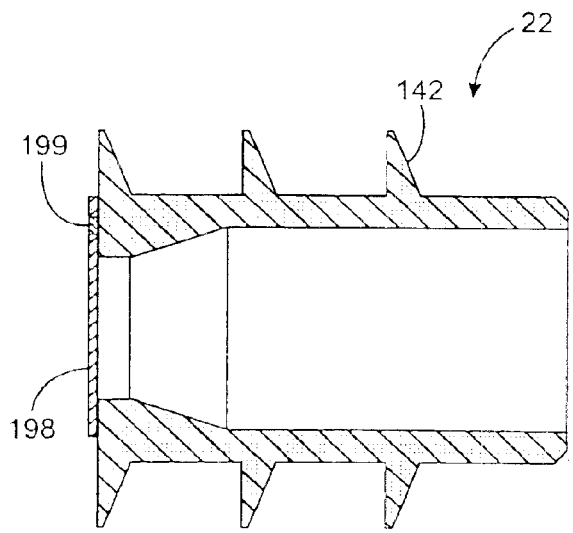
FIG. 38 is a cross-sectional view of the flap valve of FIG. 36.

Referring to FIGS. 33 and 34, still another flow control element 22 is shown. The device has a valve 189 which has at least three leaflets 191 which engage one another in the closed position. Referring to FIGS. 35 and 36, still another device is shown having a flap valve 193. The flap valve 193 deflects to permit expiratory air to pass. The flap valve 193 is preferably made of an elastomeric material. The flap valve 193 is attached to a support strut 192 extending across an open end 194 of the body 196. The body 196 has the sealing portion 142 which is preferably formed by ribs extending around the body 196. Referring to FIGS. 37 and 38, another flap valve 198 is shown. The flap valve 198 is attached to the body at hinge 199.

Figure 39:
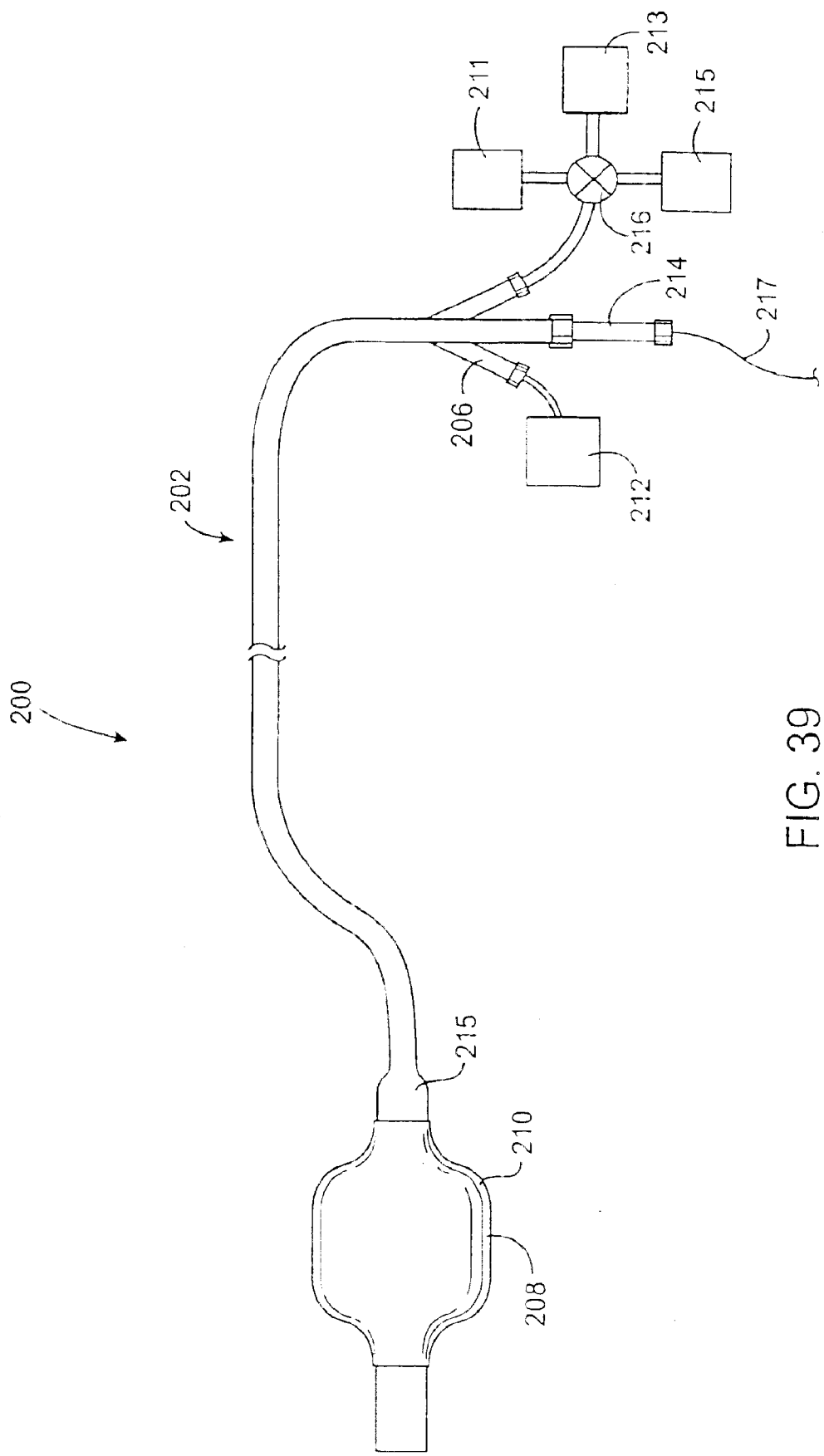
FIG. 39 shows a system for performing pulmonary procedures.
Figure 40:
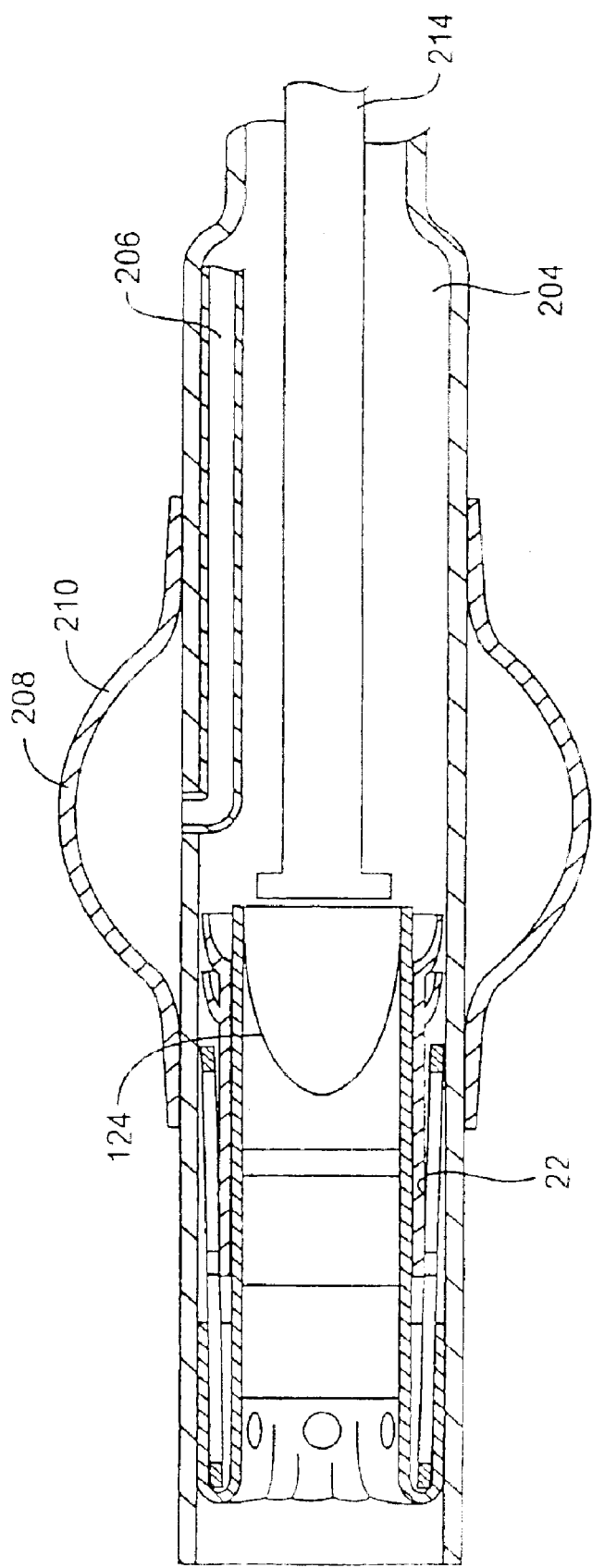
FIG. 40 is a cross-sectional view of the distal end of the system of FIG. 39.

Referring to FIGS. 39 and 40, another system 200 for deploying a device to a pulmonary location is shown. The system 200 is, of course, useful for delivering any of the devices described herein or any other suitable device. The system 200 includes a delivery element 202 having a first lumen 204 and a second lumen 206. The delivery element 202 also has an expandable member 208, such as a balloon 210, which is in fluid communication with the second lumen 206 for inflating the balloon 210 with a source of inflation fluid or gas 212. The device is loaded into the end of the delivery element 202 and a pusher 214 may be used to move the device, such as the device of FIGS. 12–16, out of the delivery element 202. The first lumen 204 has an enlarged end which forms a capsule 215 which contains the device. The element 202 may also be advanced over a guidewire 217 or the like in a conventional manner.

The delivery element 202 may also be used to remove air, and even fluid if necessary, from the isolated portion of the lung. The expandable member 208 is expanded to isolate a portion of the lung and suction is applied to deflate the lung. The isolated portion of the lung may be deflated with the device contained within the delivery element 202 or may be deflated after delivery of the device. An advantage of using the valves of the present invention is that air can be drawn through the valve even after the valve has been deployed. Referring to FIG. 40, the valve 124 also may remain operational even when in the collapsed position. Thus, the isolated portion of the lung may also be suctioned when the device is contained in the first lumen. The second lumen 206 of the delivery element 202 may be substantially independent of the outer wall of the delivery element 202 so that the stiffness of the device is reduced as compared to an integrally formed multi-lumen device. The second lumen 206 is formed by a separate tube passing through the first lumen 204. In another aspect of the invention, the delivery element 202 has an outer diameter which is 80–120%, more preferably 90–110%, of the minimum placement size of the device.

Figure 41:
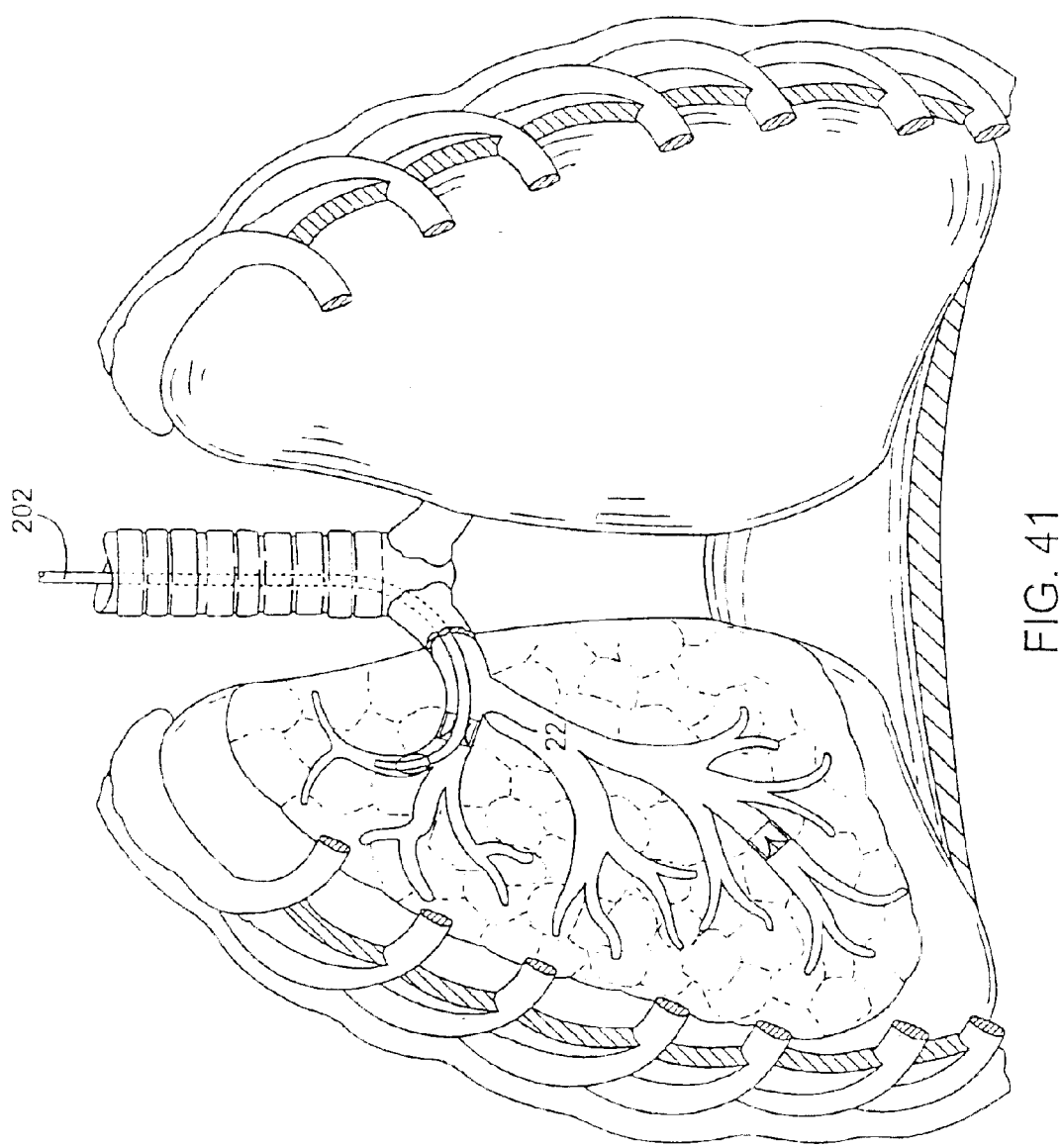
FIG. 41 illustrates access of the isolated portion of the lung through the flow control element of the present invention.
Figure 42:
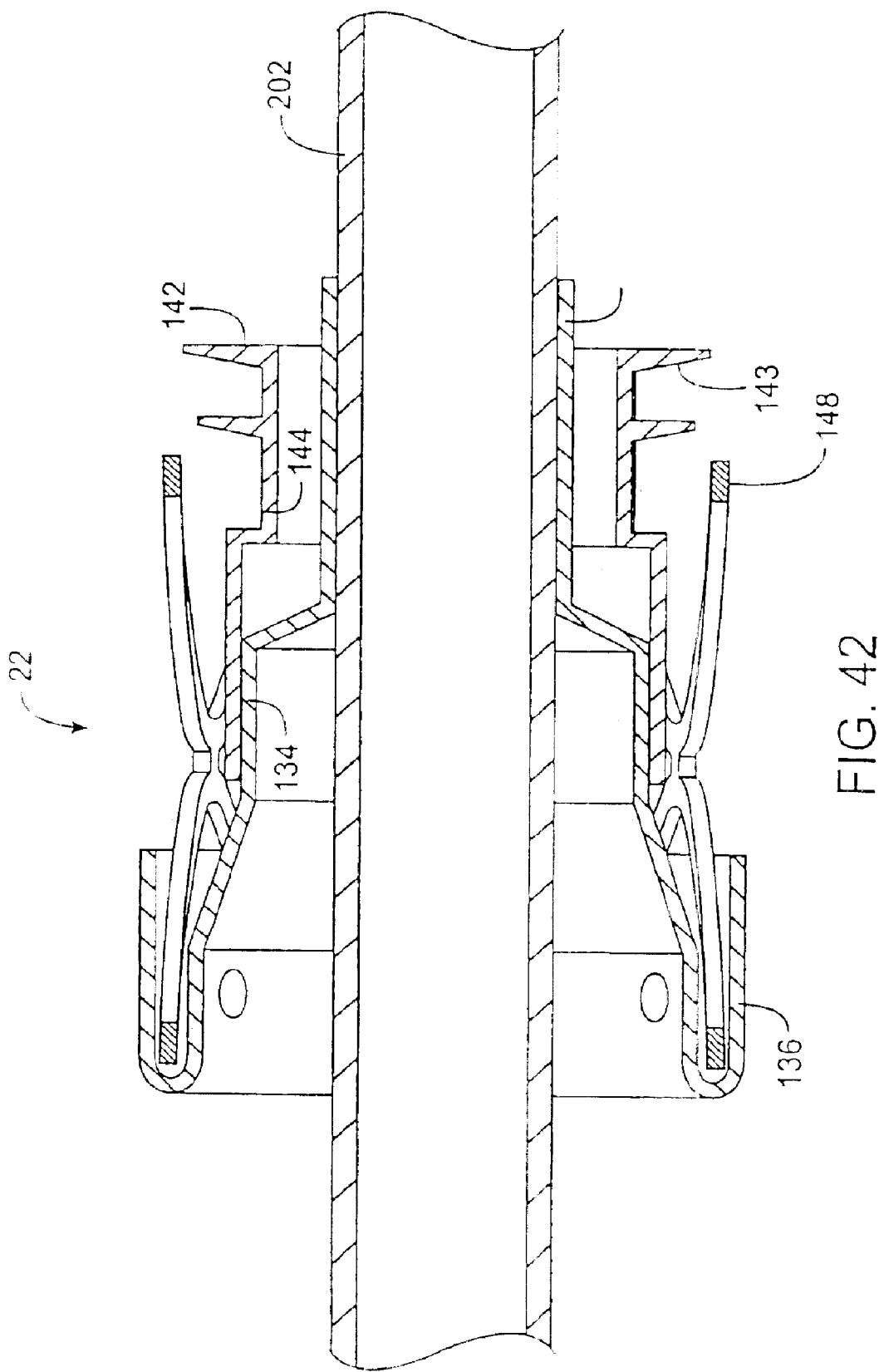
FIG. 42 shows a device passing through the flow control element of FIGS. 12–15 with the valve sealing around the device.

Referring now to FIGS. 39, 41 and 42, the isolated portion of the lung may be accessed after implantation of a device for subsequent medical treatments. For example, the valve may be penetrated with the delivery device 202, or similar device, to deliver and/or evacuate gas or liquid. The device is coupled to a source of fluid 211, such as an antibiotic or antisurfactant, which is delivered and, if necessary, evacuated from the lung. A gas, such as an antibiotic gas, may also be delivered from a source of gas 213 to the isolated area to reach distal portions of the isolated area. Finally, the device 202 may be coupled to a vacuum source 215 for deflating the isolated portion or evacuating mucous or other fluids from the isolated portion of the lung. A valve 216 is provided for selectively coupling the first lumen 204 to any of the source of fluid 211, gas 213 or vacuum 215.

Referring to FIG. 42, the device 202 may form a tight seal with the valve 124 so that the isolated portion remains deflated during the procedure. Alternatively, the device 202 may have the expandable element 208, such as the balloon 210, for occluding the pulmonary passageway on either side of the valve 124 to achieve isolation at any particular location in the pulmonary passageway distal or proximal to the valve 124.

An advantage of the present invention is that the isolated portion may be deflated after implantation of the valve without penetrating the valve. The device may be positioned proximal to the valve and the expandable element expanded to occlude the pulmonary passageway. Suction is then applied through the device so that a low pressure area develops between the valve and occluding member. When the pressure differential is large enough, the valve will open to vent and deflate the isolated portion of the lung. This process can be continued in a controlled manner until the desired amount of deflations is achieved or when a target pressure has been reached. When suction is stopped, the valve will close to isolate part of the lung.

After deployment of the valve, the delivery device, or other suitable device, may also be used as a diagnostic tool. For example, the balloon may be deflated momentarily so that the isolated area between the balloon and valve increases in pressure. If the pressure decreases after the balloon is inflated again it may indicate that the valve is not sealing properly since the air may be passing around or through the valve and into the isolated portion. An alternative diagnostic would be to pressurize the space between the valve and expandable member. The pressure response can then be monitored to determine if the valve provides an adequate seal.

The devices and valves of the present invention provide the ability to prevent inflation of diseased areas of the lung while also permitting venting of these portions of the lung. The valves preferably open with a relatively small pressure differential across the valve. For example, the valves preferably open with a pressure differential of no more than 10 inches water more preferably no more than 5 inches water and most preferably no more than 1 inch water. Although the valves and valve elements of the present invention may open with relatively small pressure differentials, the valves and valve elements may also have higher opening pressures. For example, the valves may also be designed to open only for high pressure events such as coughing. For such valves, the opening pressure, or differential pressure, is at least 25 inches water but still no more than 120 inches water. In accordance with a method of the present invention, coughing may be induced to increase the driving force and respiratory pressure to vent the isolated portions of the lung.

The flow control elements of the invention permit the diseased tissue to gradually deflate, either under the patient's own power or by applying relatively gentle suction for a given period of time. The suction may be applied intermittently or continuously by any suitable means. For example, a suction catheter could be passed through the flow control element in the bronchiole and into the distal tissue. The flow control element, for example, a valve member, would preferably seal around the catheter in order to prevent fluid moving distally past the valve.

The invention thus provides significant benefits as it permits fluid to be evacuated from the alveoli without collapsing the floppy walls of the narrow airways leading to them, problem with common lung diseases such as emphysema and COPD, as discussed above. Accordingly, the invention facilitates removal of more fluid from the diseased lung tissue than prior art approaches, the effect of which is more pleural space available to the healthy lung tissue.

In addition, as noted above, using the invention to deflate the diseased lung tissue for a selected period of time., e.g., one month, may have beneficial results on the tissue by temporarily removing it from the respiratory circuit. The flow control element is preferably removed before the tissue begins to necrose, but is left in place a sufficiently long enough time that the tissue will not revert to its floppy, toneless state when the element is removed. Stated otherwise, it may be possible to use the invention as a means for repairing (rather than removing or obliterating) diseased lung tissue, either by controlling the fluid flow in the lung tissue or by controlling the fluid flow in combination with delivering one or more substances.

For example, some possible substances with which the invention may be used include gene therapy or angiogenesis factors for lung repair or re-establishment of tissue elasticity; growth factors; anti-growth or anti-angiogenesis factors (or substances to cause necrosis or apoptosis) to prevent re-establishment of air and blood flow; antibiotics to prevent infection; anti-inflammatory agents including steroids and cortisones; sclerosing drugs or materials to promote rapid healing, for example, to allow earlier removal of the flow control element; agents for absorbing remaining fluids; and sealing substances for enhancing isolation of the diseased tissue.

The portion of the lung being treated may de deflated over time through repeated natural inhalation and exhalation with the flow control element in place. Alternatively or additionally, a vacuum source may be coupled to the flow control element to draw fluid out of the diseased tissue in the manner discussed above. This deflation of the diseased portion may be performed alone or in conjunction with delivering biological substances. The pressures used to suction the lung portion are preferably low to avoid collapsing the walls of the narrow airways.

In the embodiments in which the flow control element comprises a valve, it may be formed of various materials and may be constructed in various manners. As an example, the valve may comprise an annulus or support ring formed of any suitable metal or synthetic material, with the valve member being formed of silicone, natural rubber, latex, polyurethane, polytetrafluoroethylene, a thermoplastic elastomer, tissue, etc. The valve member may be integral with the support ring or it may be a separate member attached thereto by suitable means, e.g., suture, adhesives, mechanical fasteners. If the flow control element comprises a stent with a valve prior art attachment methods may be used. For example, see U.S. Pat. No. 5,954,766, the content of which is incorporated herein in reference.

The specific characteristics of the flow control element may be varied depending on the particular application. It may be desirable to provide multiple flow control elements with valve members that require different exhale pressures to open, for example, in order to allow treatment of patients who generate different exhalation pressures. The different flow control elements could be provided in a kit and be distinguished from each other based on required opening force, size, material, etc. The kit could include a color or other coding system to indicate these factors.

The flow control elements of the invention are preferably constructed so as to require a relatively low opening force in order to allow fluid flow in the first direction. Emphysema patients typically exhale a small quantity of low-pressure fluid. The invention preferably allows any such fluid to escape via the flow control element in the hollow structure. As such, the flow control element is designed to open and allow flow in the first direction in response to any positive pressure generated by the patient. Put another way, as long as some pressure differential exists between the distal lung tissue and the proximal portion of the bronchiole, the flow control element will open to allow fluid to escape the tissue. It will nonetheless be recognized that the particular force required to open the flow control element may be varied depending on exhalation pressures associated with the intended patient population.

It will be appreciated that features of the various preferred embodiments of the invention may be used independently or in conjunction with one another, while the illustrated methods and devices may be modified or combined in whole or in part. The inventive devices may include removable or detachable components, and may comprise disposable or reusable components, or a combination of disposable and reusable components. Likewise, it will be understood that the invention may be practiced with one or more of the steps specifically illustrated and described herein modified or omitted.

It should also be recognized that the invention is not limited to treating lung diseases as is shown in the Figures, although that is a preferred application. The invention may be used in any pulmonary or non-pulmonary procedure in which it is desirable to allow fluid flow in a first direction and control fluid flow in a second, different direction within a hollow structure. Finally, it will be understood that although a minimally invasive, endobronchial approach is shown in the Figures, other approaches may used, for example, an open surgical procedure using a median sternotomy, a minimally invasive procedure using a mini thoracotomy, or a still less invasive procedure using one or more ports or openings in the thorax, etc.

The preferred embodiments of the invention are described above in detail for the purpose of setting forth a complete disclosure and for sake of explanation and clarity. It will be readily understood that the scope of the invention defined by the appended claims will encompass numerous changes and modifications.

What is claimed is:

1. A method of controlling air flow in a pulmonary passageway, comprising the steps of:
providing a flow control element having a valve, the valve having first and second lips which engage one another when the valve is in a closed position;
advancing the flow control element through a patient's pulmonary system;
releasing the flow control element at a pulmonary site to isolate a portion of the patient's lung, the valve permitting air flow in an expiratory direction and preventing air flow in an expiratory direction.

2. The method of claim 1, wherein:
the providing step is carried out with the first lip being stiffer than the second lip, the first lip biasing the second lip toward the closed position.

3. The method of claim 1, wherein:
the providing step is carried out with the first and second lips being curved when viewed from an end of the lips.

4. The method of claim 1, wherein:
the providing step is carried out with the first and second lips forming a duckbill valve.

5. The method of claim 1, wherein:
the providing step is carried out with the first and second lips forming a heimlich valve.

6. A method of controlling air flow in a pulmonary passageway, comprising the steps of:
providing a flow control element having a valve, the flow control element having a valve body with a sealing portion which seals against the wall of the pulmonary passageway;
advancing the flow control element through a patient's pulmonary system;
releasing the flow control element at a pulmonary site to isolate a portion of the patient's lung, the valve permitting air flow in an expiratory direction and preventing air flow in an inspiratory direction.

7. The method of claim 6, wherein:
the releasing step is carried out with the sealing portion sealing against the wall of the pulmonary passageway until an opening pressure differential is achieved wherein the sealing portion opens to permit air to pass in the same direction as the valve.

8. A The method of claim 6, wherein:
the providing step is carried out with the sealing portion being made of a resilient material.

9. The method of claim 6, wherein:
the providing step is carried out with the sealing portion being a ring.

10. The method of claim 9, wherein:
the providing step is carried out with at least two rings.

11. The method of claim 10, wherein:
the rings have different sizes to seal different size locations.

12. The method of claim 6, wherein:
the providing step is carried out with the ring having a helical shape.

13. The method of claim 12, further comprising the step of: rotating the valve so that the ring anchors the device.

14. A method of controlling air flow in a pulmonary passageway, comprising the steps of:
providing a flow control element having a valve, the flow control element having a body mounted to an expandable support structure;
advancing the flow control element through a patient's pulmonary system;
releasing the flow control element at a pulmonary site to isolate a portion of the patient's lung, the valve permitting air flow in an expiratory direction and preventing air flow in an inspiratory direction.

15. The method of claim 14, wherein:
the providing step is carried out with the support structure having an exposed portion not covered by the body.

16. A method of controlling air flow in a pulmonary passageway, comprising the steps of:
providing a flow control element having a valve, the flow control element having a plurality of flexible bristles extending from the outer surface;
advancing the flow control element through a patient's pulmonary system;
releasing the flow control element at a pulmonary site to isolate a portion of the patient's lung, the valve permitting air flow in an expiratory direction and preventing air flow in an inspiratory direction, the bristles engaging the wall of the pulmonary passageway.

17. The method of claim 16, wherein:
the releasing step is carried out with the bristles being angled to preferentially anchor the valve relative to forces exerted in an expiratory direction.

18. The method of claim 16, wherein:
the providing step is carried out with at least 10 bristles.

19. A method of controlling air flow in a pulmonary passageway, comprising the steps of:
providing a flow control element having a valve, the valve being a valve selected from the group consisting of poppet, ball, duckbill, heimlich, flap and leaflet;
advancing the flow control element through a patient's pulmonary system;
releasing the flow control element at a pulmonary site to isolate a portion of the patient's lung, the valve permitting air flow in an expiratory direction and preventing air flow in an inspiratory direction.

20. A method of controlling air flow in a pulmonary passageway, comprising the steps of:
providing a flow control element having a valve, the valve having a valve structure;
advancing the flow control element through a patient's pulmonary system;
releasing the flow control element at a pulmonary site to isolate a portion of the patient's lung, the valve permitting air flow in an expiratory direction and preventing air flow in an inspiratory direction, the releasing step being carried out so that the valve structure cooperates with a portion of the wall of the passageway, the valve structure being positioned against the portion of the wall in a closed position and being spaced apart from the wall when in an open position.

21. The method of claim 20, wherein:
the providing step is carried out with the valve structure being a resilient portion positioned against the wall.

22. The method of claim 20, wherein:
the providing step is carried out with the valve structure being a ring.

23. The method of claim 20, wherein:
the providing step is carried out with the valve structure being formed by a number of independent sections which each have an open position and a closed position.

24. A method of controlling air flow in a pulmonary passageway, comprising the steps of:
providing a flow control element having a valve, the valve being generally conical;
advancing the flow control element through a patient's pulmonary system;
releasing the flow control element at a pulmonary site to isolate a portion of the patient's lung, the valve permitting air flow in an expiratory direction and preventing air flow in an inspiratory direction.

25. A method of controlling air flow in a pulmonary passageway, comprising the steps of:
providing a flow control element having a valve, the flow control element having a body, the body being integrally formed with the valve;
advancing the flow control element through a patient's pulmonary system;

releasing the flow control element at a pulmonary site to isolate a portion of the patient's lung, the valve permitting air flow in an expiratory direction and preventing air flow in an inspiratory direction.

26. A method of controlling air flow in a pulmonary passageway, comprising the steps of:

providing a flow control element having a valve, the valve having a support structure with the valve mounted to the support structure;

advancing the flow control element through a patient's pulmonary system;

releasing the flow control element at a pulmonary site to isolate a portion of the patient's lung, the valve permitting air flow in an expiratory direction and preventing air flow in an inspiratory direction.

27. A method of controlling air flow in a pulmonary passageway, comprising the steps of:

providing a flow control element having a valve, the flow control element having a large end and a small end;

advancing the flow control element through a patient's pulmonary system;

releasing the flow control element at a pulmonary site to isolate a portion of the patient's lung, the valve permitting air flow in an expiratory direction and preventing air flow in an inspiratory direction.

28. A method of controlling air flow in a pulmonary passageway, comprising the steps of:

providing a flow control element having a valve, the valve being a slit valve;

advancing the flow control element through a patient's pulmonary system;

releasing the flow control element at a pulmonary site to isolate a portion of the patient's lung, the valve permitting air flow in an expiratory direction and preventing air flow in an inspiratory direction.

29. The method of claim 28, wherein:

the providing step is carried out with the valve being generally conical.

30. A method of controlling air flow in a pulmonary passageway, comprising the steps of:

providing a flow control element having a valve with a sealant on an exterior surface of the flow control element;

advancing the flow control element through a patient's pulmonary system;

releasing the flow control element at a pulmonary site to isolate a portion of the patient's lung, the valve permitting air flow in an expiratory direction and preventing air flow in an inspiratory direction.

31. The method of claim 30, wherein:

the providing step is carried out with the sealant being an adhesive which seals a space between the flow control element and pulmonary wall.

32. The method of claim 30, wherein:

the providing step is carried out with the sealant being a flowable substance which conforms to the shape of the pulmonary site.

33. A method of controlling air flow in a pulmonary passageway, comprising the steps of:

providing a flow control element having a valve, the valve having first and second lips and reinforcing elements extending along lateral edges of the lips;

advancing the flow control element through a patient's pulmonary system;

releasing the flow control element at a pulmonary site to isolate a portion of the patient's lung, the valve permitting air flow in an expiratory direction and preventing air flow in an inspiratory direction.

34. A method of controlling air flow in a pulmonary passageway, comprising the steps of:

providing a flow control element having a valve, the valve opening upon a pressure differential of no more than 10 inches of water;

advancing the flow control element through a patient's pulmonary system;

releasing the flow control element at a pulmonary site to isolate a portion of the patient's lung, the valve permitting air flow in an expiratory direction and preventing air flow in an inspiratory direction.

35. A method of controlling air flow in a pulmonary passageway, comprising the steps of:

providing a flow control element having a valve, the valve opening upon a pressure differential of no more than 5 inches water;

advancing the flow control element through a patient's pulmonary system;

releasing the flow control element at a pulmonary site to isolate a portion of the patient's lung, the valve permitting air flow in an expiratory direction and preventing air flow in an inspiratory direction.

36. A method of controlling air flow in a pulmonary passageway, comprising the steps of:

providing a flow control element having a valve, the valve opening upon a pressure differential of no more than 1 inch water;

advancing the flow control element through a patient's pulmonary system;

releasing the flow control element at a pulmonary site to isolate a portion of the patient's lung, the valve permitting air flow in an expiratory direction and preventing air flow in an inspiratory direction.

37. The method of claim 19, wherein the providing step is carried out with the flow control element having a sealing portion which seals against the wall of the pulmonary passageway.

38. The method of claim 37, wherein the releasing step is carried out with the sealing portion sealing against the wall of the pulmonary passageway until an opening pressure differential is achieved wherein the sealing portion opens to permit air to pass in the same direction as the valve.

* * * * *

UNITED STATES PATENT AND TRADEMARK OFFICE
CERTIFICATE OF CORRECTION

PATENT NO. : 6,904,909 B2
DATED : June 14, 2005
INVENTOR(S) : Deem et al.

It is certified that error appears in the above-identified patent and that said Letters Patent is hereby corrected as shown below:

Title page,
Item [12], "Andreas et al." should read as -- Deem et al. --
Item [75], Inventors, "Bernard H. Andreas, Redwood City, CA (US); Sunmi Chew, San Jose, CA (US); "Anton J. Fields," San Francisco, CA (US); Ronald R. Hundertmark, San Mateo, CA (US); Alan R. Rapacki, Redwood City, CA (US); Peter M. Wilson, Foster City, CA (US)" should read as -- Mark E. Deem, Mountain View, CA (US); Bernard H. Andreas, Redwood City, CA (US); Sunmi Chew, San Jose, CA (US); Antony J. Fields, San Francisco, CA (US); Ronald French, Santa Clara, CA (US); Hanson S. Gifford, III, Woodside, CA (US); Ronald R. Hundertmark, San Mateo, CA (US); Alan R. Rapacki, Redwood City, CA (US); Douglas S. Sutton, Pacifica, CA (US); Peter M. Wilson, Foster City, CA (US) --
Item [56], References Cited, FOREIGN PATENT DOCUMENTS, "EP 01/28433 A1 4/2001" should read as -- WO 01/28433 A1 4/2001 --;
OTHER PUBLICATIONS,
"1L Jishi et al., "Selective Bronchial Occlusion for Treatment of Bullous Interstitial Emphysema and Bronchopleural Fistula." J. of Pediatric Surgery, 29:12, 1994: 1545-1547." should read as -- Al Jishi et al., "Selective Bronchial Occlusion for Treatment of Bullous Interstitial Emphysema and Bronchopleural Fistula." J. of Pediatric Surgery, 29:12, 1994: 1545-1547. --

Column 17,
Line 29, should read as:
8. The method of claim 6, wherein:
the providing step is carried out with the sealing portion being made of a resilient material.

Signed and Sealed this

Ninth Day of August, 2005

JON W. DUDAS
*Director of the United States Patent and Trademark Office*

UNITED STATES PATENT AND TRADEMARK OFFICE
CERTIFICATE OF CORRECTION

PATENT NO. : 6,904,909 B2
APPLICATION NO. : 10/303318
DATED : June 14, 2005
INVENTOR(S) : Deem et al.

It is certified that error appears in the above-identified patent and that said Letters Patent is hereby corrected as shown below:

Col. 16 claim 1. should read as follows:
A method of controlling air flow in a pulmonary passageway, comprising the steps of: providing a flow control element having a valve, the valve having first and second lips which engage one another when the valve is in a closed position; advancing the flow control element through a patient's pulmonary system; releasing the flow control element at a pulmonary site to isolate a portion of the patient's lung, the valve permitting air flow in an expiratory direction and preventing air flow in an expiratory inspiratory direction.

Signed and Sealed this

Twenty-ninth Day of December, 2009

David J. Kappos
*Director of the United States Patent and Trademark Office*

UNITED STATES PATENT AND TRADEMARK OFFICE
CERTIFICATE OF CORRECTION

PATENT NO.         : 6,904,909 B2                                    Page 1 of 1
APPLICATION NO. : 10/303318
DATED              : June 14, 2005
INVENTOR(S)        : Deem et al.

It is certified that error appears in the above-identified patent and that said Letters Patent is hereby corrected as shown below:

Col. 16 claim 1, lines 53-63, should read as follows:
A method of controlling air flow in a pulmonary passageway, comprising the steps of: providing a flow control element having a valve, the valve having first and second lips which engage one another when the valve is in a closed position; advancing the flow control element through a patient's pulmonary system; releasing the flow control element at a pulmonary site to isolate a portion of the patient's lung, the valve permitting air flow in an expiratory direction and preventing air flow in an expiratory inspiratory direction.

This certificate supersedes the Certificate of Correction issued December 29, 2009.

Signed and Sealed this

Nineteenth Day of January, 2010

David J. Kappos
*Director of the United States Patent and Trademark Office*

UNITED STATES PATENT AND TRADEMARK OFFICE
CERTIFICATE OF CORRECTION

PATENT NO. : 6,904,909 B2
APPLICATION NO. : 10/303318
DATED : June 14, 2005
INVENTOR(S) : Deem et al.

It is certified that error appears in the above-identified patent and that said Letters Patent is hereby corrected as shown below:

Col. 16 claim 1, lines 53-63, should read as follows:
A method of controlling air flow in a pulmonary passageway, comprising the steps of: providing a flow control element having a valve, the valve having first and second lips which engage one another when the valve is in a closed position; advancing the flow control element through a patient's pulmonary system; releasing the flow control element at a pulmonary site to isolate a portion of the patient's lung, the valve permitting air flow in an expiratory direction and preventing air flow in an inspiratory direction.

This certificate supersedes the Certificates of Correction issued December 29, 2009 and January 19, 2010.

Signed and Sealed this

Fifteenth Day of June, 2010

David J. Kappos
*Director of the United States Patent and Trademark Office*